(12) United States Patent
March et al.

(10) Patent No.: US 11,236,305 B2
(45) Date of Patent: *Feb. 1, 2022

(54) METHOD FOR ISOLATING AND CULTURING ADIPOSE STROMAL CELLS

(71) Applicant: Keith Leonard March, Carmel, IN (US)

(72) Inventors: Keith Leonard March, Carmel, IN (US); Jalees Rehman, Willowbrook, IL (US)

(73) Assignee: Keith Leonard March, Newberry, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/273,059

(22) Filed: Feb. 11, 2019

(65) Prior Publication Data

US 2019/0169573 A1    Jun. 6, 2019

Related U.S. Application Data

(60) Continuation of application No. 15/396,672, filed on Jan. 1, 2017, now abandoned, which is a continuation of application No. 14/322,233, filed on Jul. 2, 2014, now abandoned, which is a continuation of application No. 13/363,399, filed on Feb. 1, 2012, now abandoned, which is a division of application No. 13/279,222, filed on Oct. 21, 2011, now abandoned, which is a division of application No. 12/569,887, filed on Sep. 29, 2009, now Pat. No. 8,067,234, which is a division of application No. 10/508,223, filed as application No. PCT/US03/08582 on Mar. 19, 2003, now abandoned.

(60) Provisional application No. 60/365,498, filed on Mar. 19, 2002.

(51) Int. Cl.
| | |
|---|---|
| *C12N 5/00* | (2006.01) |
| *C12N 5/0775* | (2010.01) |
| *C12N 5/077* | (2010.01) |
| *C12N 5/0793* | (2010.01) |
| *A61K 35/12* | (2015.01) |

(52) U.S. Cl.
CPC ......... *C12N 5/0667* (2013.01); *C12N 5/0619* (2013.01); *C12N 5/0653* (2013.01); *A61K 35/12* (2013.01); *C12N 2501/105* (2013.01); *C12N 2501/11* (2013.01); *C12N 2501/115* (2013.01); *C12N 2501/165* (2013.01); *C12N 2506/08* (2013.01); *C12N 2506/13* (2013.01); *C12N 2506/1384* (2013.01)

(58) Field of Classification Search
USPC ........................................................... 435/325
See application file for complete search history.

(56) References Cited

U.S. PATENT DOCUMENTS

| | | | | |
|---|---|---|---|---|
| 6,153,432 A * | 11/2000 | Halvorsen | ........... | A61L 27/3804 435/377 |
| 6,391,297 B1 * | 5/2002 | Halvorsen | ............... | A61P 43/00 424/93.7 |
| 6,413,513 B1 * | 7/2002 | Holaday | ............ | A61K 38/4853 424/130.1 |
| 6,555,374 B1 * | 4/2003 | Gimble | ................ | C12N 5/0667 435/371 |
| 7,078,230 B2 * | 7/2006 | Wilkison | .............. | C12N 5/0667 435/325 |
| 7,176,023 B2 * | 2/2007 | Kaufman | ............... | C12N 5/069 435/325 |
| 8,067,234 B2 * | 11/2011 | March | .................. | C12N 5/0667 435/325 |
| 2003/0166273 A1 * | 9/2003 | Kaufman | ............... | C12N 5/069 435/366 |
| 2004/0077031 A1 * | 4/2004 | Wang | .................. | G01N 33/5011 435/23 |
| 2004/0121457 A1 * | 6/2004 | Castellon | ........... | G01N 33/5064 435/325 |
| 2004/0121968 A1 * | 6/2004 | Ljubimov | .......... | G01N 33/5008 514/43 |
| 2005/0173315 A1 * | 8/2005 | Bosch | ................. | A61M 1/3603 210/97 |
| 2005/0271738 A1 * | 12/2005 | Simon | .................... | A61K 33/42 424/520 |

OTHER PUBLICATIONS

Kawamoto (Circulation, 2001, vol. 103, p. 634-637).*
Kalka (PNAS, 2000, vol. 97, p. 3422-3427).*
Gronthos (Journal of Cellular Physiology, 2001, vol. 189, p. 54-63).*
Gimble (Organogenesis, Jan. 2013, vol. 9, No. 1, p. 3-10).*
Feng, Cell Stem Cell, 2009, vol. 4, p. 301-312.*

* cited by examiner

*Primary Examiner* — Michael C Wilson
(74) *Attorney, Agent, or Firm* — Reichel Stohry Dean LLP; Mark C. Reichel; Natalie J. Dean

(57) ABSTRACT

Methods of producing stem cell conditioned media to treat mammalian injuries or insults. In at least one embodiment of a method for isolating non-endothelial adipocyte-depleted stromal cells of the present disclosure, the method comprises, comprising dissociating subcutaneous adipose tissue isolated from a mammal into a cell suspension, removing adipocytes from said cell suspension, resulting in a non-endothelial adipocyte-depleted cell suspension, and culturing the non-endothelial adipocyte-depleted cell suspension in a media containing growth factors VEGF, bFGF, EGF, and IGF, such that a mixed population of cells comprising a first population of further differentiated non-endothelial adipocyte-depleted CD34+/VE-cadherin– cells and a second population of further differentiated non-endothelial adipocyte-depleted CD34+/VE-cadherin+ cells are obtained and expanded.

11 Claims, 18 Drawing Sheets

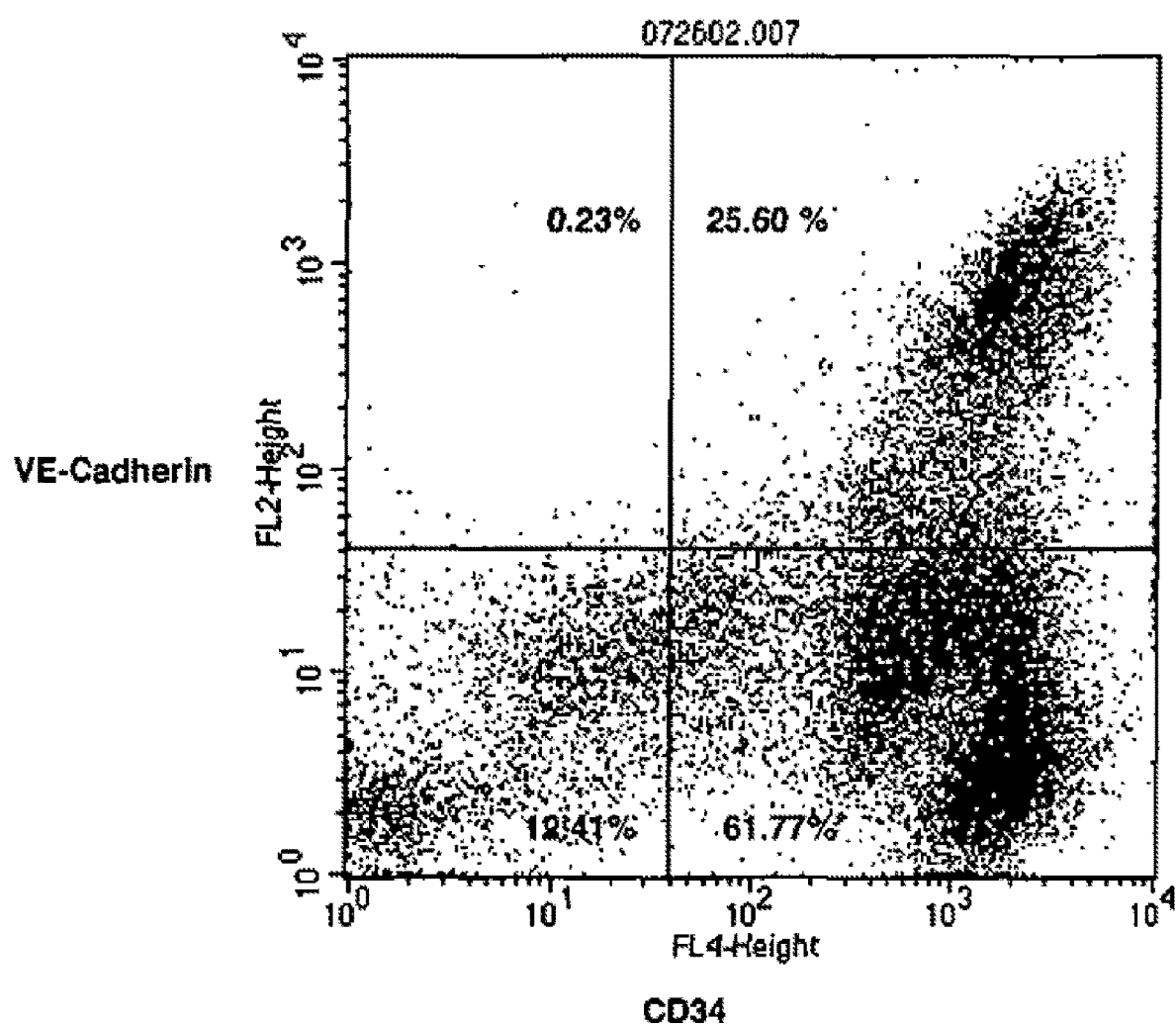

Muscle-derived cells     Adipose-derived cells

METHOD FOR ISOLATING AND CULTURING ADIPOSE STROMAL CELLS

PRIORITY

The present application is related to, claims the priority benefit of, and is a continuation application of, U.S. patent application Ser. No. 15/396,672, filed Jan. 1, 2017, now abandoned, which is related to, claims the priority benefit of, and is a continuation application of, U.S. patent application Ser. No. 14/322,233, filed Jul. 2, 2014, now abandoned, which is related to, claims the priority benefit of, and is a continuation application of, U.S. patent application Ser. No. 13/363,399, filed Feb. 1, 2012, now abandoned, which is related to, claims the priority benefit of, and is a continuation-in-part application of, U.S. patent application Ser. No. 13/279,222, filed Oct. 21, 2011, now abandoned, which is related to, claims the priority benefit of, and is a divisional application of, U.S. patent application Ser. No. 12/569,887, filed Sep. 29, 2009 and issued as U.S. Pat. No. 8,067,234 on Nov. 29, 2011, which is related to, claims the priority benefit of, and is a divisional application of, U.S. patent application Ser. No. 10/508,223, filed Jun. 23, 2005, now abandoned, which is related to, claims the priority benefit of, and is a U.S. § 371 National Stage Application of, International Patent Application Serial No. PCT/US2003/008582, filed Mar. 19, 2003, which is related to, and claims the priority benefit of U.S. Patent Application Ser. No. 60/365,498, filed Mar. 19, 2002. The contents of each of these applications are hereby incorporated by reference in their entirety into this disclosure.

BACKGROUND

The present disclosure relates to the fields of cardiology, vascularization, and molecular biology. More specifically, methods are provided for isolating stem cells from adipose tissue, optionally inducing the stem cells to secrete endogenous or exogenously provided growth factors, and re-administering such stem cells to a patient for therapeutic benefit.

Several publications and patent documents are cited throughout the specification in order to describe the state of the art to which this disclosure pertains. Each of these references is incorporated herein as though set forth in full.

Coronary artery disease (CAD) is a major cause of morbidity and mortality, requiring bypass surgery or angioplasty in almost 1,000,000 patients/year in the USA. While some of these patients form collateral vessels as alternative pathways for blood supply, thus ameliorating or preventing ischemic myocardial damage, many do not form the vascular networks to sufficiently compensate for the loss of the original blood supply. Accordingly, many patients could be helped by the development of compositions and methods which would accelerate natural processes of post-natal collateral vessel formation. Such approaches are broadly referred to as "therapeutic angiogenesis", and encompass both angiogenesis (which strictly speaking refers to capillary sprouting) and arteriogenesis (the maturation and enlargement of existing vessels) (Isner J. M. and Asahara T., J Clin Invest. (1999) 103:1231-1236; van Royen N. et al., Cardiovasc Res. (2001) 49:543-553.)

An emerging therapeutic approach is the use of stem and progenitor cell transplantation to improve angiogenesis. Endothelial progenitor cells (EPCs) are cells present in bone marrow or peripheral blood which co-express stem and progenitor cell markers like CD34 or AC133, as well as endothelial markers like VE-Cadherin and VEGF-Receptor-2 (KDR) (Rafii S., J Clin Invest. (2000) 105:17-19). EPCs and hematopoietic stem cells (HSCs) are thought to be derived from a common "hemangioblast" precursor (Ribatti D. et al., J Hematother Stem Cell Res. (2000) 9:13-19; Choi K., J Hematother Stem Cell Res. (2002) 11:91-101; Eichmann A. et al., J Hematother Stem Cell Res. (2002) 11:207-214). Interestingly, the cell surface marker CD34 is only found on either hematopoietic stem/progenitor cells or endothelial cells (Rafii S., J Clin Invest. (2000) 105:17-19), which may be a reflection of the common origin of these two cell lineages. In addition to the shared "hemangioblastic" ancestry between HSCs and endothelial cells, HSCs have also been suggested to trans-differentiate into either endothelial progenitor cells or mature endothelial cells (Kang H. J. et al., Br J Haematol. (2001) 113:962-969; Quirici N. et al., Br J Haematol. (2001) 115:186-194; Gehling U. M. et al., Blood. (2000) 95:3106-3112). The recent discovery of circulating smooth muscle progenitor cells, and the potential of HSCs to differentiate into smooth muscle cells (Sata M. et al., Nat Med. (2002) 8:403-409; Simper D. et al., Circulation (2002) 106:1199-1204) may suggest yet another novel and intriguing link between the hematopoietic and vascular cell lineages, now in the context of smooth muscle cells.

Animal studies using hindlimb ischemia or myocardial ischemia models in immune deficient rodents have demonstrated that transplantation of about $10^6$ peripheral blood derived EPCs (Kawamoto A. et al., Circulation (2001) 103:634-637; Kalka C. et al., Proc Natl Acad Sci USA (2000) 97:3422-3427) can result in increased angiogenesis. Remarkably, labeled peripheral blood derived EPCs appear to home preferentially to ischemic areas and incorporate into foci of neovascularization (Kawamoto A. et al., Circulation (2001) 103:634-637; Kalka C. et al., Proc Natl Acad Sci USA (2000) 97:3422-3427). In addition to the above-mentioned studies on peripheral blood-derived cells, EPCs derived from bone marrow, unpurified bone marrow mononuclear cells, and HSCs have also been shown to enhance angiogenesis or show endothelial differentiation in vivo in a variety of animal models of ischemia (Kocher A. A. et al., Nat Med. (2001) 7:430-436; Shintani S. et al., Circulation (2001) 103:897-903; Fuchs S. et al., J Am Coll Cardiol (2001) 37:1726-1732; Kamihata H. et al., Circulation (2001) 104:1046-1052; Orlic D. et al., Proc Natl Acad Sci USA (2001) 98:10344-10349; Jackson K. A. et al., J Clin Invest. (2001) 107:1395-1402).

Transplantation of hematopoietic stem cells (HSCs) into patients with myelodysplastic disorders or following myeloablative radiochemotherapy is the most widespread application of stem cell therapy. HSCs are characterized by surface markers like CD34, and constitute less than 0.5-1% of the bone marrow (Gunsilius E. et al., Biomed Pharmacother. (2001) 55:186-194), which is currently the primary source of transplantable HSCs in the clinical setting. The limited availability of HLA-compatible siblings (less than 30%) (Tabbara I. A. et al., Arch Intern Med. (2002) 162: 1558-1566) has resulted in frequent use of non-HLA-compatible siblings as donors. Although recently there has been some success in the reduction of complications following allogeneic transplantation of HSCs, chronic graft versus host disease and engraftment failure of allogeneic cells remains a significant clinical problem (Tabbara I. A. et al., Arch Intern Med. (2002) 162:1558-1566). Autologous stem cell transplantation circumvents these complications, however, autologous cells from the bone marrow or peripheral blood may be contaminated by malignant cells (Hahn U. and To L.

B., In: Schindhelm K., Nordon R. eds. Ex vivo Cell Therapy. San Diego, Calif.: Academic Press; (1999) 99-126).

While the concept of using autologous peripheral blood derived EPCs in patients seems attractive, based on animal studies, one would need 12 liters of blood from a patient to isolate enough cells to achieve a pro-angiogenic effect (Iwaguro H. et al., Circulation. (2002) 105:732-738). This amount of blood is not readily available in a clinical setting. Human studies that have used bone marrow cell transplantation in ischemic patients (Strauer B. E. et al., Dtsch Med Wochenschr. (2001) 126:932-938; Tateishi-Yuyama E. et al., Lancet. (2002) 360:427-435) suggest that human angiogenic cell therapy requires at least cell numbers of $10^7$ to $10^9$, depending on the degree of stem cell purity as well as the optimal delivery method.

The discovery of pluripotent cells in the adipose tissue (Zuk P. A. et al., Tissue Engineering. (2001) 7:211-228) has revealed a novel source of cells that may be used for autologous cell therapy to regenerate tissue. The pluripotent cells reside in the "stromal" or "non-adipocyte" fraction of the adipose tissue; they were previously considered to be pre-adipocytes, i.e. adipocyte progenitor cells, however recent data suggests a much wider differentiation potential. Zuk et al. were able to establish differentiation of such subcutaneous human adipose stromal cells (ASCs) in vitro into adipocytes, chondrocytes and myocytes (Zuk P. A. et al., Tissue Engineering. (2001) 7:211-228). These findings were extended in a study by Erickson et al., which showed that human ASCs could differentiate in vivo into chondrocytes (Erickson et al., Biochem Biophys Res Commun. (2002) 290:763-769) following transplantation into immune-deficient mice. More recently, it was demonstrated that human ASCs were able to differentiate into neuronal cells (Safford K. M. et al., Biochem Biophys Res Commun. (2002) 294: 371-379).

Given the many applications of stem cell therapy, a need exists in the art for providing a more abundant and practical source for such stem cells, and for enhancing the potential therapeutic benefit and route of administration of these cells.

BRIEF SUMMARY

In accordance with the present disclosure, isolated, adipose tissue derived stromal cells are provided. The cells of the present disclosure may be induced to express at least one characteristic of a variety of cell types including but not limited to cardiac cells, endothelial cells, smooth muscle cells, dopaminergic neuronal cells, hematopoietic cells, or hepatic cells. Further, the cells may be induced to express a growth factor including but not limited to vascular endothelial growth factor (VEGF), hepatocyte growth factor (HGF), granulocyte-colony stimulating factor (G-CSF), and basic fibroblast growth factor (bFGF), with or without subsequent cell culture.

Another object of the present disclosure is to provide a method of promoting angiogenesis, cardiomyogenesis, or regeneration of hematopoietic cells in which the cells of the present disclosure are delivered to a patient. The cells may be delivered by methods which include but are not limited to retrograde coronary venous infusion, retrograde delivery to other tissues, direct injection into target tissue, intra-arterial or intra-coronary infusion via a catheter, and systemic intravenous administration.

Another object of the disclosure is a method for isolating adipose derived stem cells, and optionally culturing the cells in a medium of interest. As a further option, these cells may be exposed to a receptor ligand cocktail including but not limited to at least one of VEGF, LIF, bFGF, IGF1, IGF2, HGF, cardiotrophin, myotrophin, nitric oxide synthase 3, tumor necrosis factor alpha, tumor necrosis factor beta, fibroblast growth factor, pleotrophin, endothelin, and angiopoietin.

In yet a further embodiment of the present disclosure, the adipose derived stromal cells may comprise an exogenous nucleic acid encoding a protein of interest.

BRIEF DESCRIPTION OF THE DRAWINGS

FIG. 5 shows flow cytometric analysis of CD-34 and VE-cadherin expression on plated adipose stromal cells.

FIG. 11C shows staining for the neuronal tau-protein (red) and nuclei staining (DAPI, blue) with confocal microscopy.

DETAILED DESCRIPTION

Figure 1A:
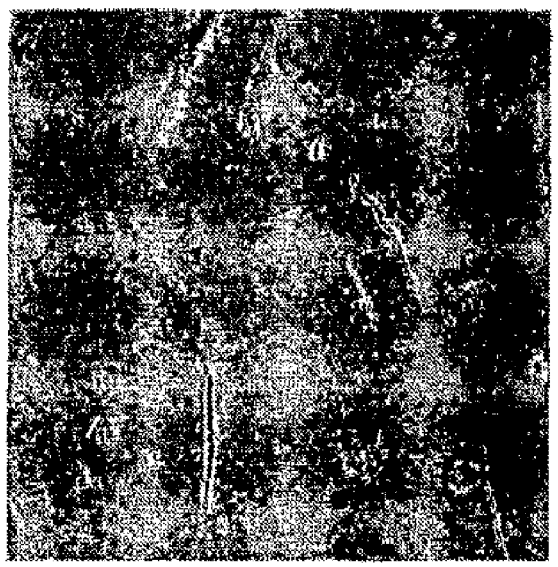
FIGS. 1A and 1B show phase contrast micrographs of sub-confluent (FIG. 1A) and confluent (FIG. 1B) cultures of human adipose stromal cells grown in EGM2MV media, at 250× magnification.

Stem cell therapies are expected to someday provide a wide range of treatment options for various diseases. However the difficulties associated with obtaining stem cells in therapeutic quantities has troubled the scientific community. As described above, stem cells from blood and/or bone marrow cannot be isolated in sufficient quantity for therapy without significant cell expansion. Further, it is difficult to find an HLA matched donor, and allogenic transplants pose a high risk of complications.

New methods of deriving stem cells from adipose tissue provide an excellent solution to these challenges. The methods disclosed herein will demonstrate that $10^5$ to $10^6$ cells that are obtained from 5-10 grams of subcutaneous tissue can be expanded 50-fold in approximately one week. Considering that the simple outpatient procedure of liposuction can often yield 1 liter of fat tissue even in non-obese patients, ASC cell numbers of $10^8$ to $10^9$ can be isolated from an individual with little or no expansion.

Furthermore, the methods disclosed herein demonstrate ways to induce these adipose stromal cells to secrete useful growth factors which can promote new tissue growth. For example, ASC's can be induced to secrete Vascular Endothelial Growth Factor (VEGF), which is known to be an effective inducer of angiogenesis.

Methods provided herein combine efficient isolation of therapeutic quantities of stem cells with inducing these stem cells to secrete growth factors such as VEGF. These cells can then be administered to a patient to promote vascularization and tissue growth in areas of ischemic damage.

I. Definitions

The following definitions are provided to facilitate an understanding of the present disclosure:

The term "autologous" implies identical nuclear genetic identity between donor cells or tissue and those of the recipient.

The term "adipose stromal cells" refers to the "non-adipocyte" fraction of adipose tissue. The cells can be fresh, or in culture. Adipose stromal cells contain pluripotent cells, which have the ability to differentiate into cell types including but not limited to adipocytes, cardiomyocytes, endothelial cells, hematopoietic cells, hepatic cells, chondrocytes, osteoblasts, neuronal cells, and myotubes. "Adipose stem cells" are cells within the adipose stromal fraction which exhibit a stem cell phenotype, such as CD45−/Sca-1+/c-kit− or CD45−/CD34+/c-kit−.

"Therapeutic quantities of stromal cells" or "therapeutic quantities of stem cells" refers to the minimum amount of stem cells which will produce a desired therapeutic effect. For example, a therapeutic quantity of VEGF secreting stem cells is the quantity which will produce therapeutically beneficial levels of angiogenesis, when administered to a patient.

"Therapeutic angiogenesis" or "therapeutic vascular growth" includes but is not limited to angiogenesis (such as capillary sprouting) and arteriogenesis (such as the maturation and enlargement of existing vessels.)

The term "regeneration" or "tissue regeneration" includes, but is not limited to the growth, generation, or reconstruction of new cells types or tissues from the ASCs of the instant disclosure. These cells types or tissues include but are not limited to endothelial cells, cardiomyocytes, hematopoietic cells, hepatic cells, adipocytes, chondrocytes, osteoblasts, neuronal cells, and myotubes. Cardiomyogenesis refers to cardiac tissue regeneration or reconstruction. Tissue regeneration also includes bone marrow repopulation using the ASCs of the present disclosure, which express hematopoietic lineage cell marker(s).

"Growth factors" are molecules which promote tissue growth, cellular proliferation, vascularization, and the like. These include, but are not limited to Vascular Endothelial Growth Factors A, B, C, D, and E (VEGF), Placental Growth Factor, Hepatocyte Growth Factor (HGF), Granulocyte-Colony Stimulating Factor, Granulocyte-macrophage Colony Stimulating Factor, Macrophage Colony Stimulating Factor, Monocyte Chemotactic Factor, TGF family, FGF family, pleiotrophin, endothelin, angiopoietins, and so forth.

"Multipotent" implies that a cell is capable, through its progeny, of giving rise to several different cell types found in the adult animal.

"Pluripotent" implies that a cell is capable, through its progeny, of giving rise to all the cell types which comprise the adult animal including the germ cells. Both embryonic stem and embryonic germ cells are pluripotent cells under this definition.

The term "transgenic" animal or cell refers to animals or cells whose genome has been subject to technical intervention including the addition, removal, or modification of genetic information. The term "chimeric" also refers to an animal or cell whose genome has modified.

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (3rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; and Animal Cells: culture and media, 1994, D. C. Darling, S. J. Morgan John Wiley and Sons, Ltd.

The term "cell line" as used herein can refer to cultured cells that can be passaged at least one time without terminating. The present disclosure relates to cell lines that can be passaged at least 1, 2, 5, 10, 15, 20, 30, 40, 50, 60, 80, 100, and 200 times. Cell passaging is defined hereafter.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the present disclosure can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel which has been supplemented with medium suitable for further cell proliferation.

The term "proliferation" as used herein in reference to cells can refer to a group of cells that can increase in number over a period of time.

The term "permanent" or "immortalized" as used herein in reference to cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells die in culture.

The term "precursor cell" or "precursor cells" as used herein can refer to a cell or cells used to establish cultured mammalian cells or a cultured mammalian cell line. A precursor cell or cells may be isolated from nearly any cellular entity.

The term "reprogramming" or "reprogrammed" as used herein can refer to materials and methods that can convert a cell into another cell having at least one differing characteristic. Also, such materials and methods may reprogram or convert a cell into another cell type that is not typically expressed during the life cycle of the former cell. For example, (1) a non-totipotent cell can be reprogrammed into a totipotent cell; (2) a precursor cell can be reprogrammed into a cell having a morphology of an EG cell; and (3) a precursor cell can be reprogrammed into a totipotent cell. An example of materials and methods for converting a precursor cell into a totipotent cell having EG cell morphology is described hereafter.

The term "isolated" as used herein can refer to a cell that is mechanically separated from another group of cells. Examples of a group of cells are a developing cell mass, a cell culture, a cell line, and an animal.

The term "non-embryonic cell" as used herein can refer to a cell that is not isolated from an embryo. Non-embryonic cells can be differentiated or nondifferentiated. Non-embryonic cells can refer to nearly any somatic cell, such as cells isolated from an ex utero animal. These examples are not meant to be limiting.

The term "differentiated cell" as used herein can refer to a precursor cell that has developed from an unspecialized phenotype to a specialized phenotype. For example, embryonic cells can differentiate into an epithelial cell lining the intestine. Materials and methods of the present disclosure can reprogram differentiated cells into totipotent cells. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

The term "asynchronous population" as used herein can refer to cells that are not arrested at any one stage of the cell cycle. Many cells can progress through the cell cycle and do not arrest at any one stage, while some cells can become arrested at one stage of the cell cycle for a period of time. Some known stages of the cell cycle are G1, S, G2, and M. An asynchronous population of cells is not manipulated to synchronize into any one or predominantly into any one of these phases. Cells can be arrested in the M stage of the cell cycle, for example, by utilizing multiple techniques known in the art, such as by colcemid exposure. Examples of methods for arresting cells in one stage of a cell cycle are discussed in WO 97/07669, entitled "Quiescent Cell Populations for Nuclear Transfer".

The terms "synchronous population" and "synchronizing" as used herein can refer to a fraction of cells in a population that are within a same stage of the cell cycle. Preferably, about 50% of cells in a population of cells are arrested in one stage of the cell cycle, more preferably about 70% of cells in a population of cells are arrested in one stage of the cell cycle, and most preferably about 90% of cells in a population of cells are arrested in one stage of the cell cycle. Cell cycle stage can be distinguished by relative cell size as well as by a variety of cell markers well known to a person of ordinary skill in the art. For example, cells can be distinguished by such markers by using flow cytometry techniques well known to a person of ordinary skill in the art. Alternatively, cells can be distinguished by size utilizing techniques well known to a person of ordinary skill in the art, such as by the utilization of a light microscope and a micrometer, for example. In a preferred embodiment, cells are synchronized by arresting them (i.e., cells are not dividing) in a discreet stage of the cell cycle.

An "exogenous nucleic acid" as used herein refers to any nucleic acid which is introduced into the ASCs of the present disclosure, and encodes a protein of interest. Specific exogenous nucleic acids encode proteins which include without limitation a Vascular Endothelial Growth Factor A, B, C, D, and E (VEGF), bFGF, IGF1, IGF2, Hepatocyte Growth Factor (HGF), Placental Growth Factor, cardiotrophin, myotrophin, nitric oxide synthases 1, 2, or 3, Granulocyte-Colony Stimulating Factor, Granulocyte-macrophage Colony Stimulating Factor, Macrophage Colony Stimulating Factor, Monocyte Chemotactic Factor, TGF family, FGF family, pleiotrophin, endothelin, angiopoietins, and genes promoting differentiation along pre-determined pathways.

The term "modified nuclear DNA" as used herein can refer to a nuclear deoxyribonucleic acid sequence of a cell of the present disclosure that has been manipulated by one or more recombinant DNA techniques. Examples of recombinant DNA techniques are well known to a person of ordinary skill in the art, which can include (1) inserting a DNA sequence from another organism (e.g., a human organism) into target nuclear DNA, (2) deleting one or more DNA sequences from target nuclear DNA, and (3) introducing one or more base mutations (e.g., site-directed mutations) into target nuclear DNA. Cells with modified nuclear DNA can be referred to as "transgenic cells" or "chimeric cells" for the purposes of the present disclosure. The phrase "modified nuclear DNA" may also encompass "corrective nucleic acid sequence(s)" which replace a mutated nucleic acid molecule with a nucleic acid encoding a biologically active, phenotypically normal polypeptide. The constructs utilized to generate modified nuclear DNA may optionally comprise a reporter gene encoding a detectable product.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

"Selectable marker" as used herein refers to a molecule that when expressed in cells renders those cells resistant to a selection agent. Nucleic acids encoding selectable marker may also comprise such elements as promoters, enhancers, translational control sequences, poly A addition signals, transcriptional termination signals and the like. Suitable selection agents include antibiotic such as kanamycin, neomycin, and hygromycin.

Methods and tools for insertion, deletion, and mutation of nuclear DNA of mammalian cells are well-known to a person of ordinary skill in the art. See, Molecular Cloning, a Laboratory Manual, 2nd Ed., 1989, Sambrook, Fritsch, and Maniatis, Cold Spring Harbor Laboratory Press; U.S. Pat. No. 5,633,067, "Method of Producing a Transgenic Bovine or Transgenic Bovine Embryo," DeBoer et al., issued May 27, 1997; and U.S. Pat. No. 5,612,205, "Homologous Recombination in Mammalian Cells," Kay et al., issued Mar. 18, 1997. These methods include techniques for transfecting cells with foreign DNA fragments and the proper design of the foreign DNA fragments such that they effect insertion, deletion, and/or mutation of the target DNA genome.

The adipose stromal cells defined herein can be altered to harbor modified nuclear or cytoplasmic DNA.

Examples of methods for modifying a target DNA genome by insertion, deletion, and/or mutation are retroviral or adeno-associated viral insertion, artificial chromosome techniques, gene insertion by electroporation, sonoporation, or chemical methods, random insertion with tissue specific promoters, homologous recombination, gene targeting, transposable elements, and/or any other method for introducing foreign DNA. Other modification techniques well known to a person of ordinary skill in the art include deleting DNA sequences from a genome, and/or altering nuclear DNA sequences. Examples of techniques for altering nuclear DNA sequences are site-directed mutagenesis and polymerase chain reaction procedures. Therefore, the present disclosure relates in part to mammalian cells that are simultaneously totipotent and transgenic. Such transgenic and totipotent cells can serve as nearly unlimited sources of donor cells for production of cloned transgenic animals.

The term "recombinant product" as used herein can refer to the product produced from a DNA sequence that comprises at least a portion of the modified nuclear DNA. This product can be a peptide, a polypeptide, a protein, an enzyme, an antibody, an antibody fragment, a polypeptide that binds to a regulatory element (a term described hereafter), a structural protein, an RNA molecule, and/or a ribozyme, for example. These products are well defined in the art.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The term "nuclear transfer" as used herein can refer to introducing a full complement of nuclear DNA from one cell to an enucleated cell. Nuclear transfer methods are well known to a person of ordinary skill in the art. See, e.g., Nagashima et al., 1997, Mol. Reprod. Dev. 48: 339-343; Nagashima et al., 1992, J. Reprod. Dev. 38: 73-78; Prather et al., 1989, Biol. Reprod. 41: 414-419; Prather et al., 1990, Exp. Zool. 255: 355-358; Saito et al., 1992, Assis. Reprod. Tech. Andro. 259: 257-266; and Terlouw et al., 1992, Theriogenology 37: 309. Nuclear transfer may be accomplished by using oocytes that are not surrounded by a zona pellucida.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the present disclosure relates to any transformation technique well known to a person of ordinary skill in the art.

The term "antibiotic" as used herein can refer to any molecule that decreases growth rates of a bacterium, yeast, fungi, mold, or other contaminants in a cell culture. Antibiotics are optional components of cell culture media. Examples of antibiotics are well known in the art. See Sigma and DIFCO catalogs.

The term "feeder cells" as used herein can refer to cells that are maintained in culture and are co-cultured with target cells. Target cells can be precursor cells, adipose stromal cells, cultured cells, and totipotent cells, for example. Feeder cells can provide, for example, peptides, polypeptides, electrical signals, organic molecules (e.g., steroids), nucleic acid molecules, growth factors (e.g., bFGF), other factors (e.g., cytokines such as LIF and steel factor), and metabolic nutrients to target cells. Certain cells may not require feeder cells for healthy growth. Feeder cells preferably grow in a mono-layer.

Feeder cells can be established from multiple cell types. Examples of these cell types are fetal cells, mouse cells, and oviductal cells. These examples are not meant to be limiting. Tissue samples can be broken down to establish a feeder cell line by methods well known in the art (e.g., by using a blender). Feeder cells may originate from the same or different animal species as precursor cells. Feeder cells can be established from fetal cells, mammalian fetal cells, and murine fetal cells.

The term "receptor ligand cocktail" as used herein can refer to a mixture of one or more receptor ligands. A receptor ligand can refer to any molecule that binds to a receptor protein located on the outside or the inside of a cell. Receptor ligands can be selected from molecules of the cytokine family of ligands, neurotrophin family of ligands, growth factor family of ligands, and mitogen family of ligands, all of which are well known to a person of ordinary skill in the art. Examples of receptor/ligand pairs are: vascular endothelial growth factor receptor/vascular endothelial growth factor, epidermal growth factor receptor/ epidermal growth factor, insulin receptor/insulin, cAMP-dependent protein kinase/cAMP, growth hormone receptor/ growth hormone, and steroid receptor/steroid. It has been shown that certain receptors exhibit cross-reactivity. For example, heterologous receptors, such as insulin-like growth factor receptor 1 (IGFR1) and insulin-like growth factor receptor 2 (IGFR2) can both bind IGF1. When a receptor ligand cocktail comprises a stimulus, the receptor ligand cocktail can be introduced to a precursor cell in a variety of manners known to a person of ordinary skill in the art.

The term "cytokine" as used herein can refer to a large family of receptor ligands well-known to a person of ordinary skill in the art. The cytokine family of receptor ligands includes such members as leukemia inhibitor factor (LIF); cardiotrophin 1 (CT-1); ciliary neurotrophic factor (CNTF); stem cell factor (SCF), which is also known as Steel factor; oncostatin M (OSM); and any member of the interleukin (IL) family, including IL-6, IL-1, and IL-12. The teachings of the present disclosure do not require the mechanical addition of steel factor (also known as stem cell factor in the art) for the conversion of precursor cells into totipotent cells.

II. Methods of Isolating Autologous Stem Cells from Adipose Tissues

In accordance with the present disclosure, it has been discovered that therapeutic quantities of autologous stem cells may be obtained from adipose tissue. Such stem cells can be obtained as described herein.

For example, adipose tissue is obtained from an animal, preferable a human, and most preferably from the patient who is the intended recipient of the therapeutic stem cells. The tissue may be obtained by numerous methods known in the art, including without limitation liposuction, and surgery. Preferably, the adipose tissue is obtained by liposuction, which is a simple, minimally invasive procedure.

In an exemplary method, following collection, adipose tissue is optionally washed, for example with saline (such as PBS) to removed loose matter. Next, the tissue is digested with an enzyme, (such as collagenase, dispase, or trypsin), and/or may also be degraded by mechanical agitation, sonic energy, thermal energy, and the like. The resultant product is then optionally filtered, and then centrifuged to separate the stromal cells from the adipose cells. Another round of washing and centrifugation may be performed in order to further purify the cells. The cells may also be sorted using flow cytometry or other cell sorting means, and further isolated. Cells so obtained exhibit stem cell markers, eg. CD34.

Other methods of isolating stem cells from adipose tissue are known in the art, and are disclosed for example in Zuk P. A. et al., Tissue Engineering (2001) 7:211-228).

III. Methods of Inducing Stem Cells to Differentiate and/or Express Growth Factors Stem cells derived from adipose tissue as set forth above may be used in many therapeutic procedures. Transgenic stem cells so obtained may also be optionally transfected at this point with a "corrective nucleic acid sequence". The stem cells so obtained are then passaged and exposed to a receptor ligand cocktail to induce differentiation into the desired cell lineage as exemplified herein below.

Tissues currently being developed from stem cells include, but are not limited to: blood vessels (Kocher A. A. et al., Nature Med. (2001) 7:430-436; Jackson K. A. et al., J. Clin. Invest. (2001) 107:1395-1402), bone (Petite H. et al., Nature Biotech. (2000) 18:959-963), cartilage (Johnstone B. et al., Clin. Orthop. (1999) 5156-5162), cornea (Tsai R. J. et al., N. Eng. J. Med. (2000) 343:86-93), dentin (Gronthos S. et al., Proc. Natl. Acad. Sci. USA (2000) 97:13625-13630), heart muscle (Klug M. G. et al., J. Clin. Invest. (1996) 98:216-224; review Boheler K. R. et al., Cir. Res. (2002) 91:189-201), liver (Lagasse E. et al., Nature Med. (2000) 6:1229-1234), pancreas (Soria B. et al., Diabetes (2000) 49:1-6; Ramiya V. K. et al., Nature Med. (2000) 6:278-282), nervous tissue (Bjorkland A., Novartis Found. Symp. (2000) 231:7-15; Lee S. H. et al., Nature Biotechnology (2000) 18:675-679; Kim J. H. et al., Nature (2002) 418:50-56), skeletal muscle (Gussoni E. et al., Nature (1999) 401:390-394), and skin (Pellegrini G. et al., Transplantation (1999) 68:868-879). Some of the tissues being generated from stem cells are described in further detail below.

Heart Muscle

The loss of cardiomyocytes from adult mammalian hearts is irreversible and leads to diminished heart function. Methods have been developed in which embryonic stem (ES) cells are employed as a renewable source of donor cardiomyocytes for cardiac engraftment (Klug, M. G. et al., J. Clin. Invest. (1996) 98:216-224). The ASC cells of the present disclosure can be similarly differentiated.

ES cells were first transfected by electroporation with a plasmid expressing the neomycin resistance gene from an .alpha.-cardiac myosin heavy chain promoter and expressing the hygromycin resistance gene under the control of the phosphoglycerate kinase (pGK) promoter. A proportion of cells comprising an activatable .alpha.-cardiac myosin heavy chain promoter will differentiate into cardiac cells. Transfected clones were selected by growth in the presence of hygromycin (200 µg/ml; Calbiochem-Novabiochem). Transfected ES cells were maintained in the undifferentiated state by culturing in high glucose DMEM containing 10% fetal bovine serum (FBS), 1% nonessential amino acids, and 0.1 mM 2-mercaptoethanol. The medium was supplemented to a final concentration of 100 U/ml with conditioned medium containing recombinant LIF.

To induce differentiation, $2\times10^6$ freshly dissociated transfected ES cells were plated onto a 100-mm bacterial Petri dish containing 10 ml of DMEM lacking supplemental LIF. Regions of cardiogenesis were readily identified by the presence of spontaneous contractile activity. For cardiomyocyte selection, the differentiated cultures were grown for 8 days in the presence of G418 (200 µg/ml; GIBCO/BRL). Cultures of selected ES-derived cardiomyocytes were digested with trypsin and the resulting single cell preparation was washed three times with DMEM and directly injected into the ventricular myocardium of adult mice.

The culture obtained by this method after G418 selection is more 99% pure for cardiomyocytes based on immunofluorescence for myosin. The obtained cardiomyocytes contained well defined myofibers and intercalated discs were observed to couple juxtaposed cells consistent with the observation that adjacent cells exhibit synchronous contractile activity. Importantly, the selected cardiomyocytes were capable of forming stable intercardiac grafts with the engrafted cells aligned and tightly juxtaposed with host cardiomyocytes. As mentioned previously the adipose stromal cells of the present disclosure can be similarly treated to generate cardiomyocytes.

Endothelial Cells

Endothelial cells are critical to neo-vascularization, and are known to secrete numerous growth factors which promote healing and expansion. Administration of endothelial cells promotes angiogenesis, resulting in increased vascularization and development. Methods of inducing stem cells to differentiate to endothelial cells are generally known in the art, and are disclosed for example, in Balconi et al., Arterioscler Thromb Vasc Biol. (2000) 20:1443-1451.

Stem cell lines were grown in the undifferentiated state either on gelatin (0.1%)-coated Petri dishes (CJ7) or on a feeder layer of STO murine fibroblasts.

To initiate cell differentiation cells were briefly trypsinized and suspended in Iscove's modified Dulbecco's medium with 15% FBS, 10 mg/mL insulin (Sigma), 100 U/mL penicillin, 100 mg/mL streptomycin, and 450 mmol/L monothioglycerol. A growth factor cocktail was added to the culture medium to optimize vascular differentiation and included: recombinant human VEGF (Peprotech Inc) at 50 ng/mL; recombinant human erythropoietin (Cilag AG), at 2 U/mL; human bFGF (Genzyme), at 100 ng/mL; and murine interleukin 6 (Genzyme), at 10 ng/mL.

Cells were seeded in bacteriological Petri dishes ($1.5\times10^4$ cells per 35-mm Petri dish) and cultured for 11 days, without further feeding, at 37° C. in an incubator with 5% $CO_2$ in air and 95% relative humidity. The cells were routinely examined for the presence of endothelium-like structures by whole-mount preparation, by using rat mAb MEC 7.46 directly against mouse PECAM as primary antibody and commercial rabbit immunoglobulins to rat immunoglobulin (DAKO) as a secondary antibody.

In some cases, endothelial cells were selected with the use of sheep anti-mouse CD31 mAb-coated magnetic beads (Dynabeads, Dynal AS). In some experiments, endothelial cell lines could be obtained without immunoselection. In those cases, after EB disaggregation, the cells were immortalized by PmT. In previous studies, it was observed that PmT specifically immortalizes endothelial cells and not any other cell type.

A suitable culture medium for stem-cell derived endothelial cells is DMEM with 20% FBS, supplemented with 2 mmol/L glutamine, 100 U/mL penicillin, 100 mg/mL streptomycin, 50 mg/mL endothelial cell growth supplement (Sigma), and 100 mg/mL heparin (Sigma) (Balconi et al., Arterioscler Thromb Vasc Biol. (2000) 20:1443-1451).

ASCs in accordance with the present disclosure can be induced to form endothelial cells in a similar fashion.

Neuronal Cells

Parkinson's disease is caused by the loss of midbrain neurons that synthesize the neurotransmitter dopamine. Delivery of dopamine-synthesizing neurons to the midbrain should alleviate the symptoms of the disease by restoring dopamine production. Stem cells obtained using the methods of the present disclosure may be differentiated into dopamine-synthesizing neurons utilizing the exemplary protocols set forth below. (Lee, S. H. et al., Nature Biotechnology, (2000) 18:675-679; Kim, J. H. et al., Nature (2002) 418:50-56).

In a murine model, mouse ES cells were first transfected by electroporation with a plasmid expressing nuclear receptor related-1 (Nurr1), a transcription factor that has a role in the differentiation of midbrain precursors into dopamine neurons and a plasmid encoding neomycin resistance. Transfected clones (Nurr1 ES cells) were then subsequently isolated by culturing the cells in G418. The Nurr1 ES cells were then expanded under cultures which prevented differentiation (e.g., growth on gelatin-coated tissue culture plates in the presence of 1,400 U/ml-I of leukemia inhibitory factor (LIF; GIBCO/BRL, Grand Island, N.Y.) in ES cell medium consisting of knockout Dulbecco's minimal essential medium (GIBCO/BRL) supplemented with 15% FCS, 100 mM MEM nonessential amino acids, 0.55 mM 2-mercaptoethanol, L-glutamine, and antibiotics (all from GIBCO/BRL)). Selection of nestin-positive cells, a marker of developmental neurons, was initiated by replacing the ES cell medium by serum-free Dulbecco's modified Eagle's medium (DMEM)/F12 (1:1) supplemented with insulin (5 µg/ml), transferrin (50 µg/ml), selenium chloride (30 nM), and fibronectin (5 µg/ml) (ITSFn) medium. After 6-10 days of selection, expansion of nestin-positive cells was initiated. Specifically, the cells were dissociated by 0.05% trypsin/0.04% EDTA, and plated on tissue culture plastic or glass coverslips at a concentration of $1.5-2\times10^5$ cells/cm2 in N2 medium modified (described in Johe K. et al., Genes Dev. (1996) 10:3129-3140), and supplemented with 1 µg/ml of laminin and 10 ng/ml of bFGF (R&D Systems, Minneapolis, Minn.) in the presence of murine N-terminal fragment of sonic hedgehog (SHH; 500 ng/ml) and murine fibroblast growth factor (FGF) 8 isoform b (100 ng/ml; both from R&D Systems). Before cell plating, dishes and coverslips were precoated with polyornithine (15 mg/ml) and laminin (1 µg/ml, both from Becton Dickinson Labware, Bedford, Mass.). Nestin-positive cells were again expanded for six days. The medium was changed every two days. Differentiation was induced by removal of basic FGF (bFGF). The differentiation medium consisted of N2 medium supplemented with laminin (1 mg/ml) in the presence of cAMP (1 µM) and ascorbic acid (200 µM, both from Sigma St. Louis, Mo.). The cells were incubated under differentiation conditions for 6-15 days.

78% of Nurr1 ES cells were found to be induced into dopamine-synthesizing, tyrosine hydroxylase (TH, 4 rate limiting enzyme in the biosynthesis of dopamine) positive neurons by the method set forth above. The resultant neurons were further characterized to express a variety of midbrain-specific markers such as Ptx3 and Engrailed 1 (En-1). The dopamine-synthesizing, TH+ cells were also grafted into a rodent model of Parkinson's disease and were shown to extend axons, form functional synaptic connections, perform electrophysiological functions expected of neurons, innervate the striatum, and improve motor asymmetry.

The ASCs of the present disclosure may be induced to form neuronal cells in a similar fashion.

Insulin-Producing Cells

An ideal treatment for diabetes is the restoration of β-cell function or mimicking the insulin secretory pattern of these cells. Insulin-secreting cells derived from stem cells have been generated by the following method and have been shown to be capable of normalizing blood glucose levels in a diabetic mouse model (Soria, B. 10 et al., Diabetes (2000) 49:1-6).

ES cells were transfected by electroporation with a plasmid expressing β-gal under the control of the human insulin regulatory region and expressing the hygromycin resistance gene under the control of the pGK promoter. Transfected clones were selected by growth in the presence of hygromycin (200 pg/ml; Calbiochem-Novabiochem). Transfected ES cells were maintained in the undifferentiated state by culturing in high glucose Dulbecco's modified Eagle's medium (DMEM) containing 10% fetal bovine serum (FBS), 1% nonessential amino acids, 0.1 mM 2-mercaptoethanol, 1 mM sodium pyruvate, 100 IU/ml penicillin, and 0.1 mg/ml streptomycin. The medium was supplemented to a final concentration of 100 U/ml with conditioned medium containing recombinant LIF.

To induce differentiation to an insulin-secreting cell line, $2 \times 10^6$ hygromycin-resistant ES cells were plated onto a 100-mm bacterial Petri dish and cultured in DMEM lacking supplemental LIF. For ES Ins/β-gal selection, the differentiated cultures were grown in the same medium in the presence of 200 µg/ml G418. For final differentiation and maturation, the resulting clones were trypsinized and plated on a 100-mm bacterial Petri dish and grown for 14 days in DMEM supplemented with 200 µg/ml G418 and 10 mM nicotinamide (Sigma), a form of Vitamin B3 that may preserve and improve beta cell function. Finally, the resulting clusters were cultured for 5 days in RPMI 1640 media supplemented with 10% FBS, 10 mM nicotinamide, 200 µg/ml G418, 100 IU/ml penicillin, 0.1 mg/ml streptomycin, and low glucose (5.6 mM).

For cell implantation, ES-derived insulin-secreting cells were washed and resuspended in RPMI 1640 media supplemented with 10% FBS, 10 mM nicotinamide, 100 IU/ml penicillin, 0.1 mg/ml streptomycin, and 5.6 mM glucose at $5 \times 10^6$ cells/ml. The mice to receive the implantation of ES-derived insulin-secreting cells were male Swiss albino mice that had diabetic conditions induced by a single intraperitoneal injection of streptozotocin (STZ, Sigma) at 200 mg/kg body weight in citrate buffer. $1 \times 10^6$ cells were injected into the spleen of mice under anesthesia.

The ES-derived insulin-secreting cells produced from this method produced a similar profile of insulin production in response to increasing levels of glucose to that observed in mouse pancreatic islets. Significantly, implantation of the ES-derived insulin-secreting cells led to the correction of the hyperglycemia within the diabetic mouse, minimized the weight loss experienced by the mice injected with STZ, and lowered glucose levels after meal challenges and glucose challenges better than untreated diabetic mice and similar to control nondiabetic mice.

The ASCs of the present disclosure may be similarly differentiated into insulin producing cells using similar methods.

Hematopoietic Cells

Hematopoietic cells are used in numerous therapeutic regimens such as replenishing bone marrow supply, or treating hematological disorders, such as anemias, thalassemias, and so forth. Stem cells can be differentiated into hematopoietic stem cells by methods known in the art, and disclosed, for example, in Howell et al., Experimental Hematology (2002) 30:915-924.

In Howell et al., CD45−Sca-1+c-kit− cells were incubated for nine days in MEM+10% HS in the presence of 5 ng/mL mSCF, mFlt-3L, and MGDF, which are cytokines. Cells were then expanded. Cells expressed increased levels of c-kit.

The in vivo repopulating potential of these cells was then assessed by transplanting $4 \times 10^4$ cells into lethally irradiated Boy J (CD45.1) recipient mice. Analysis of peripheral blood after 4 months revealed that freshly isolated cells exhibited 7.9%+/−2.9% chimerism in recipient mice. A mathematical derivation of fold expansion of engraftment potential of cultured cells, relative to fresh cells revealed that these cytokine cultured cells have a 5 fold increase in relative hematopoietic repopulating potential.

The ASCs of the present disclosure may be similarly differentiated into hematopoietic cells, and used therapeutically to treat hematopoietic disorders.

The recently described ability to genetically manipulate human ES cells should allow for the rapid isolation of highly uniform and singularly differentiated cells (Eiges R. et al., Current Biol. (2001) 11:514-518). A potential method to this end would be to employ a similar method to that described above for murine ES cells in which antibiotic resistance genes or selectable marker genes are expressed under cell specific promoters. Alternatively, cell-type specific transcription factors or any other cell-type specific factors found to drive cell-type specific differentiation can be expressed.

IV. Administration of Adipose Derived Stem Cells for Therapeutic Benefit

The adipose derived stem cells of the present disclosure can be used in a wide array of therapeutic procedures. These therapies include administration of adipose stem cells, administration of stem cells which secrete growth factors such as VEGF, and stem cells which have been transfected to express a desired therapeutic molecule.

These molecules may be administered by a variety of methods, including retrograde coronary venous delivery, direct injection, arterial infusion via catheter, systemic administration via IV, and so forth.

Methods of delivery of molecules to the heart via retrograde coronary venous delivery are generally known in the art and are described for example in Boekstegers P. et al., Gene Ther (2000) 7:232-240, Herity N. A., Cathet. Cardiovasc. Intervent. (2000) 51:358-363, Suzuki et al., Circulation (2000) 111:359-364, and Yock et al., U.S. Pat. No. 6,346,098. The injection of cells via RCVD can be at rates which achieve pressures of about 30-400 mm Hg, most preferably about 50-150 mm Hg.

Retrograde coronary venous delivery is a suitable method for delivery of other types of stem cells having therapeutic benefit. Such stem cells include without limitation bone marrow derived stem cells, peripheral blood mononuclear derived stem cells, and skeletal tissue derived myocytes.

Methods of direct injection comprise primarily direct infusion, ideally by hypodermic needle to the site where increased vascularization is desired. For example, adipose stem cells of the present disclosure may be administered via intramuscular injection, to a tissue where angiogenesis is desired.

Methods of infusion via indwelling catheter generally comprise placement of an indwelling catheter to a region where stem cell therapy would be beneficial, and administration of the adipose stem cells of the present disclosure through such a catheter.

The following non-limiting examples are provided to further illustrate the present disclosure.

Example 1

Figure 1B:
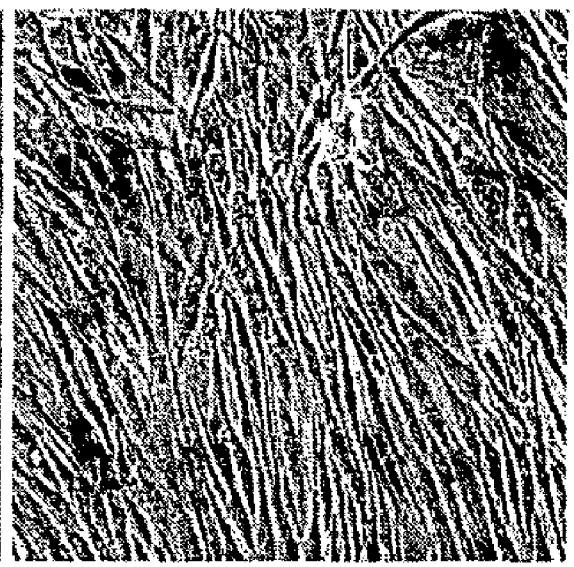
Figure 2:
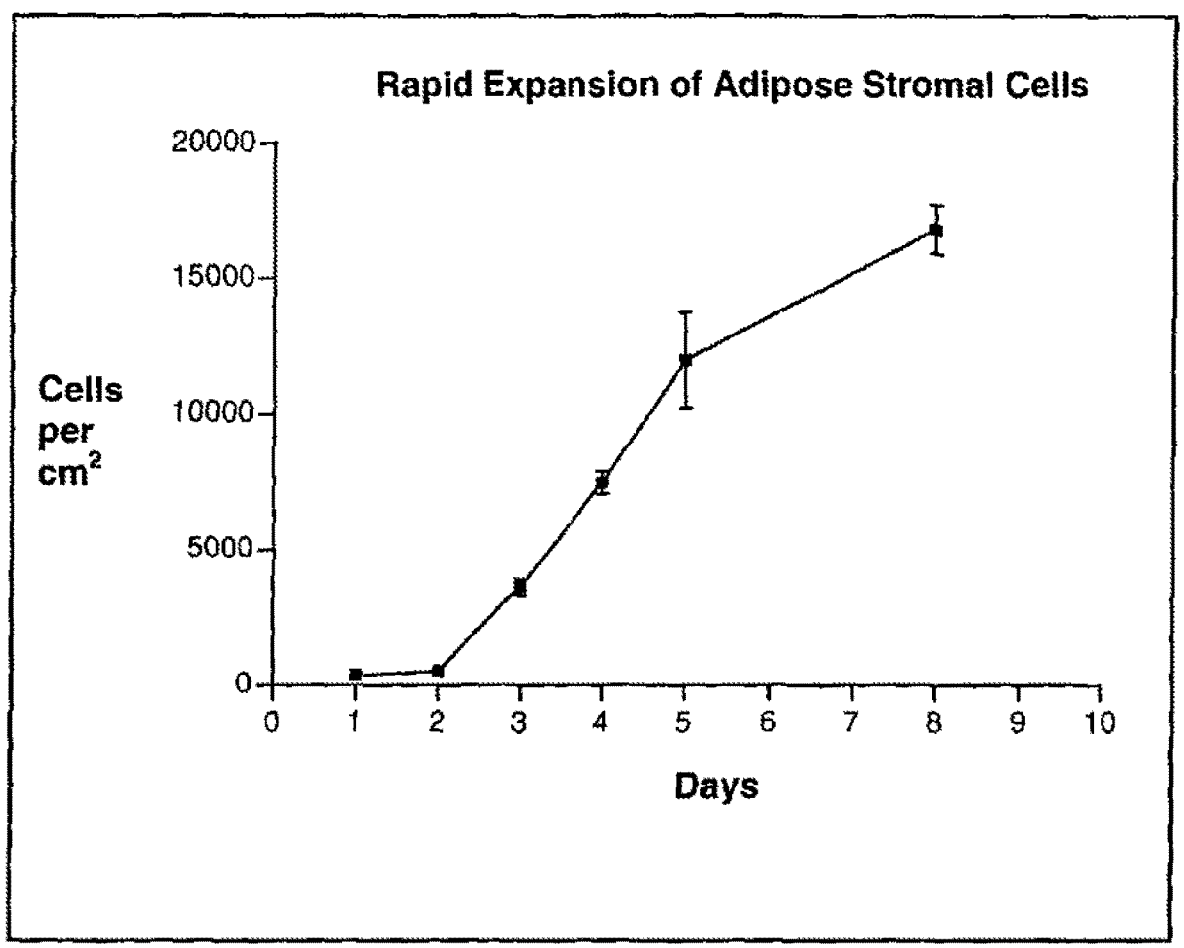
FIG. 2 is a graph showing growth of human subcutaneous adipose stromal cells.

Isolation and Characterization of Stem Cells from Adipose Tissue
Isolation of Stem Cells from Adipose Tissue To isolate adipose stromal cells (ASCs) subcutaneous adipose tissue (5-15 grams) was obtained from obese patients undergoing a gastroplasty procedure. The tissue was suspended in PBS and dissected into smaller pieces using a scalpel. Collagenase (Worthington Biochemical) was then added to the suspension and placed in a shaker at 37° C. for approximately 90 minutes. The digested sample was filtered through a 750 micron Nitex filter and a 50 micron filter, and rinsed with Dulbecco's Modified Eagle Media (DMEM) with 10% Fetal Bovine Serum (FBS). The filtered suspension was centrifuged at 200 g for 5 minutes and the top layer consisting of adipocytes was discarded. After a second spin at 300 g for 5 minutes, any remaining adipocytes in the top layer were again discarded. The cell pellet was re-suspended in red cell lysis buffer and centrifuged at 300 g after 5-10 minutes of incubation at 37° C. This cell pellet consisted of adipose stromal cells and was re-suspended in the desired media. Adipose stromal cells (ASCs) were plated on tissue culture flasks at densities ranging from 1000 to 10,000 cells per $cm^2$. Non-adherent cells were discarded on the following day. The majority of ASCs attach to the flask and these adherent cells (FIG. 1) can be expanded in either DMEM media with 10% FBS or in EGM2MV media (Clonetics), which contains the growth factors VEGF, bFGF, EGF, IGF and 5% FBS. Cells cultured in EGM2MV media, for example, can be expanded 50-fold in 8 days (FIG. 2) with their growth rate decreasing when they reach confluency. ASCs continue to have a high proliferative activity when they are passaged. ASCs were also isolated from porcine and murine adipose tissue using similar isolation and culture protocols.

These experiments demonstrate that ASCs can be readily isolated and rapidly expanded ex vivo from relatively small amounts of adipose tissue, thus indicating that autologous ASCs may be used to advantage in research and clinical protocols. Human cardiovascular cell therapy studies suggest that $10^8$ to $10^9$ autologous cells may be required for clinical applications. Considering the fact that liposuction can yield up to 3 liters of subcutaneous fat tissue in a single outpatient procedure, such cell numbers can be easily obtained from patients with little or no expansion.

Expression of Stem Cell Markers on ASCs

Figure 3:
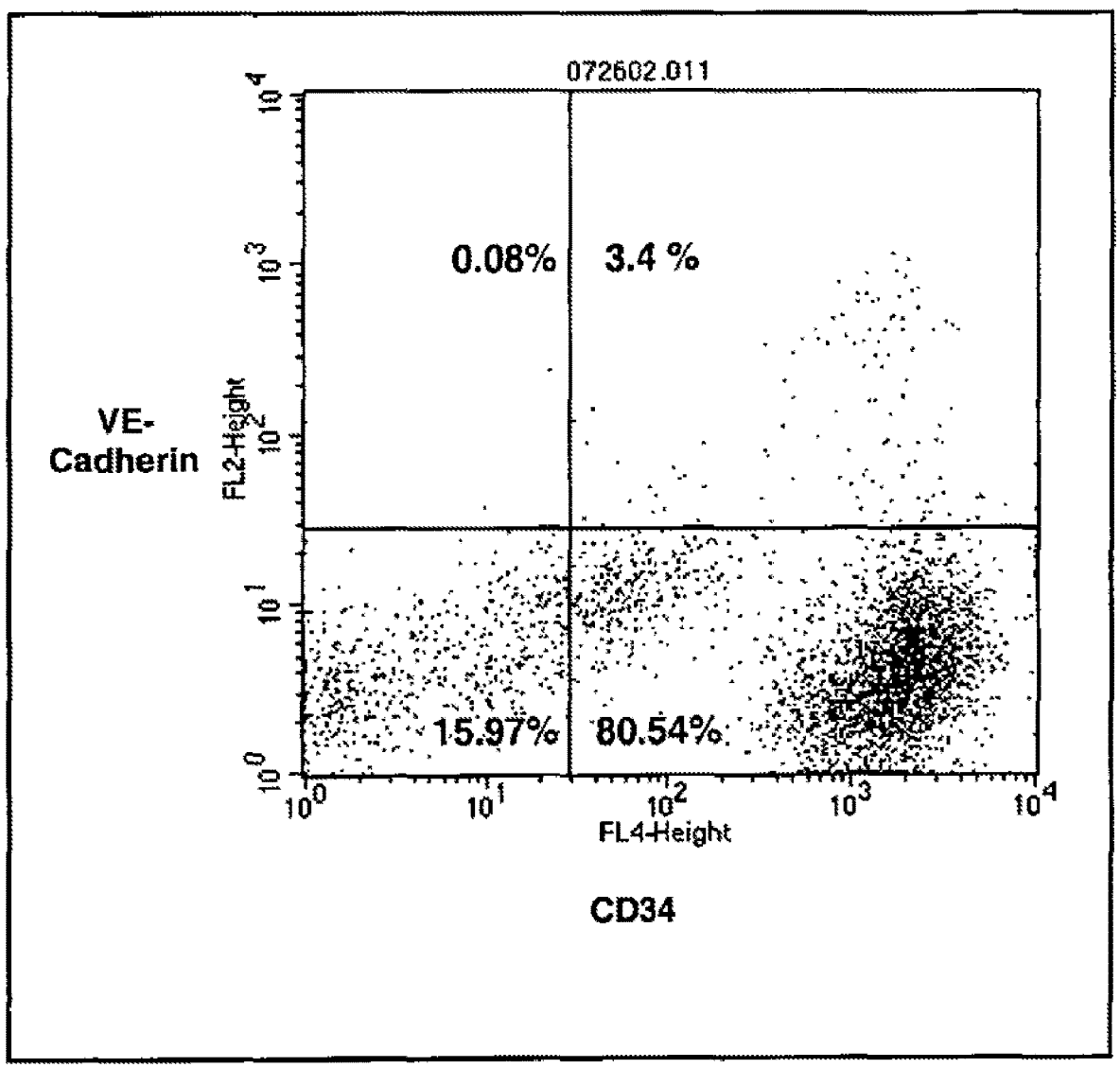
FIG. 3 shows flow cytometric analysis of fresh human subcutaneous adipose stromal cells.

To evaluate the expression of the stem cell marker CD-34, adipose stromal cells were freshly isolated from human adipose tissue and labeled with fluorescent antibodies against CD34 (BD Biosciences). As CD 34 is also expressed on mature endothelial cells and endothelial progenitor cells, the isolated cells were co-labeled with an antibody directed against human VE-cadherin (BD Biosciences), a highly specific marker of endothelial cells (Rafii S., J Clin Invest. (2000) 105:17-19). Data from a representative experiment is shown in FIG. 3. The results indicate that the majority of cells are CD34+/VE-cadherin−, thus suggesting that most human adipose tissue derived stromal cells are non endothelial CD34-positive stem or progenitor cells. The human adipose stromal cell fraction also contains a small but distinct population of CD34+/VE-cadherin+ cells, which may represent either mature endothelial cells or endothelial progenitor cells.

Figure 4:
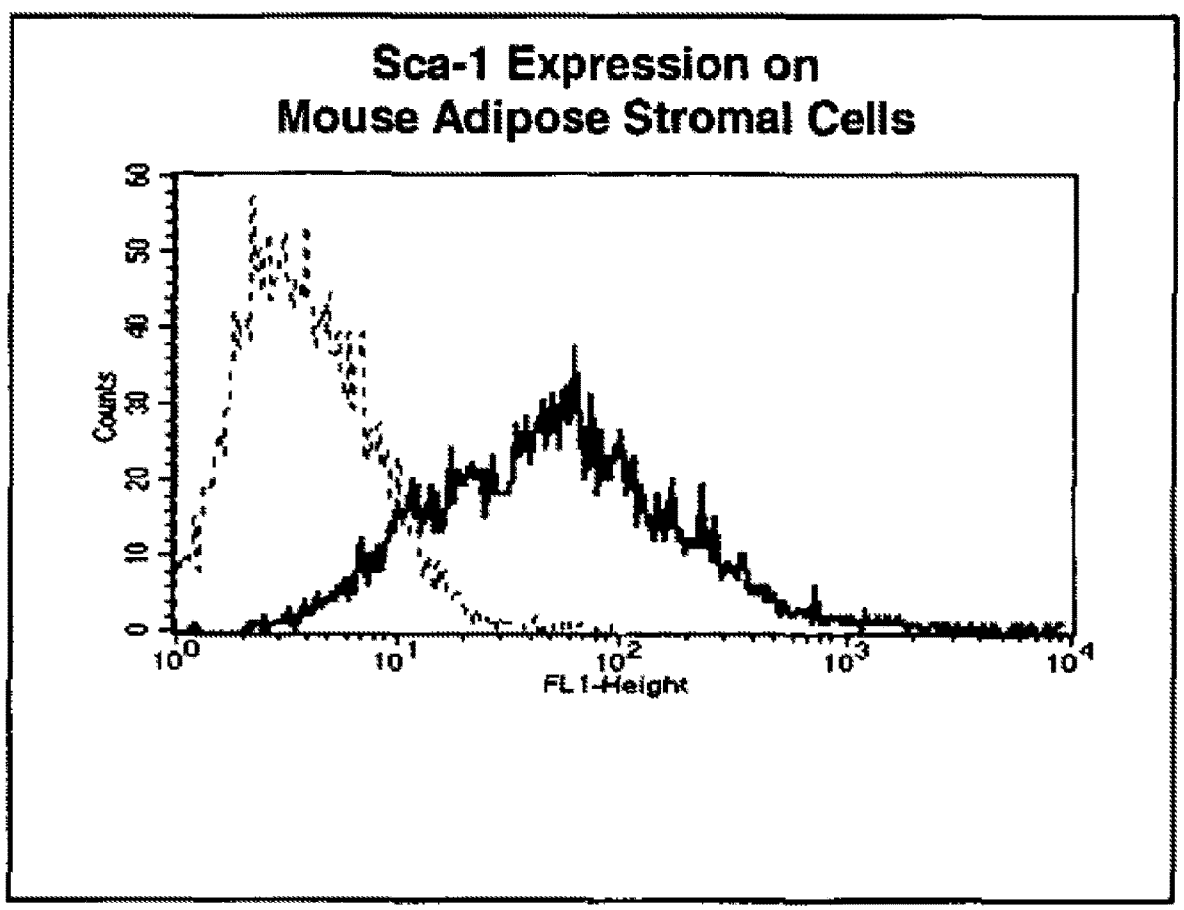
FIG. 4 shows flow cytometric analysis of Sca-1 expression (green) and the corresponding isotype control (pink.)

To determine whether the expression of stem cell markers could also be found on adipose stromal cells in the mouse, murine ASCs were isolated from mice using the same protocol that was used for human ASC isolation. Murine ASCs were cultured, expanded in DMEM/F12 media with 10% fetal bovine serum and passaged when confluent. The passaged cells were finally detached with EDTA at confluence and subsequently labeled with an antibody directed against the specific murine stem cell marker Sca-1 (Stem Cell Antigen-1). As shown in FIG. 4, greater than 70% of cultured murine ASCs express the stem cell marker Sca-1. The high level of expression of CD34 in human ASCs and of Sca-1 on murine ASCs complements the data on ASC differentiation potential (Zuk P. A. et al., Tissue Engineering (2001) 7:211-228; Erickson et al., Biochem Biophys Res Commun. (2002) 290:763-769; Safford K. M. et al., Biochem Biophys Res Commun. (2002) 294:371-379) and provides evidence that ASCs have stem cell characteristics.

Example II

Differentiation of Adipose Derived Stromal Cells
ASCs can Develop a Vascular Phenotype A major pathway by which ASCs can enhance angiogenesis is by differentiation of ASCs into a vascular cell phenotype. Since ASCs are already known to differentiate into a number of cell types like muscle, bone and neural cells, it was evaluated whether ASCs can develop phenotypes that correspond to either vascular endothelial cells or vascular smooth muscle cells. Plated adherent human ASCs were evaluated by flow cytometry for the expression of the stem cell marker CD34 and the endothelial marker VE-Cadherin, (FIG. 5). While the majority of cells are still CD34+/VE-Cadherin−, there has emerged a substantial proportion of cells that are CD34+/VE-Cadherin+; this finding has been replicated consistently with samples from several donors. This is in contrast to freshly isolated ASCs, which express minimal VE-Cadherin (FIG. 3), prior to plating. The appearance of a CD34+/VE-Cadherin+ cell population suggests that differentiation towards an endothelial phenotype may have occurred. This experiment also demonstrates that the adherent ASC population continues to express high levels of the stem cell marker CD34 both in conjunction with the expression of VE-cadherin, as well as in a VE-cadherin-negative population. In parallel experiments (data not shown), it was found the human ASC population began to express an additional endothelial marker, the VEGF receptor-2, (KDR or flk-1) following passage, whereas they did not express this marker at detectable levels when freshly isolated; this finding supports the interpretation of direction towards an endothelial lineage.

Figure 6A:
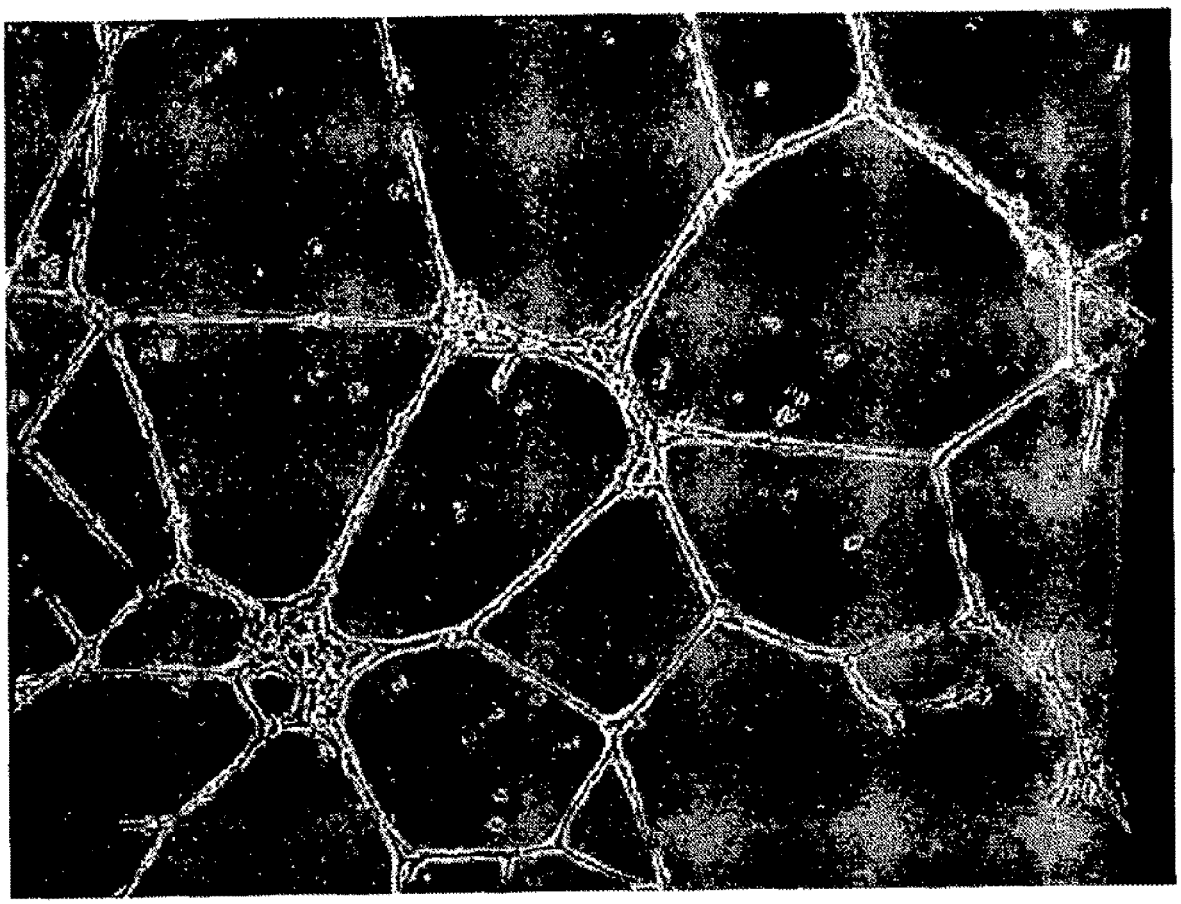
FIGS. 6A and 6B show human aortic endothelial cells (FIG. 6A) and human adipose stromal cells (FIG. 6B) plated overnight on Matrigel.
Figure 6B:
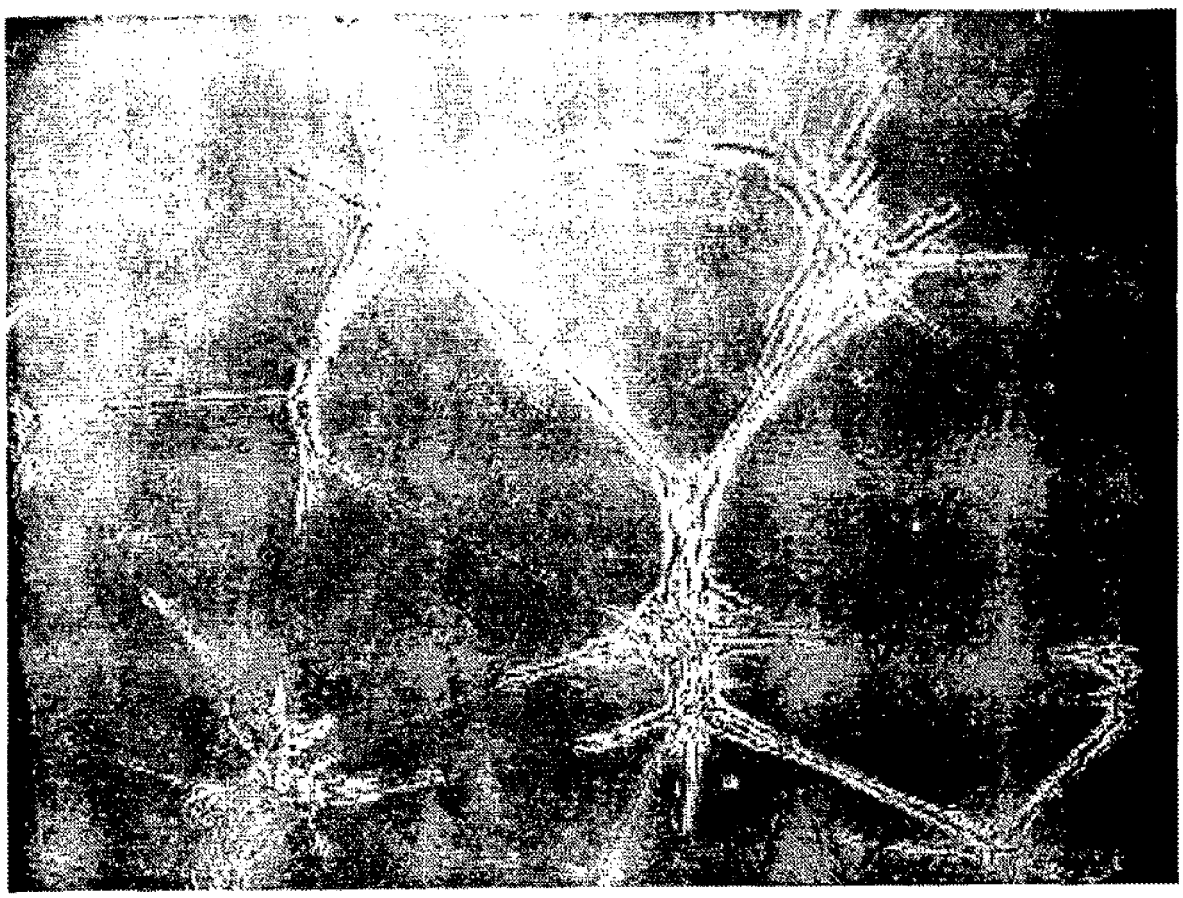

To examine whether ASCs can also manifest typical endothelial behavior in vitro, their phenotype on Matrigel was determined. Mature endothelial cells when plated overnight on Matrigel (BD Biosciences) form tube- and cord-like structures, reminiscent of a capillary network. Human subcutaneous ASCs that had been cultured in EGM2MV media on Matrigel overnight were plated, and the non-adherent cells were discarded the following day. Human aortic endothelial cells were also plated as a positive control in a separate Matrigel well (FIG. 6). The endothelial cells formed the expected tube and cord-like structures. Interestingly, ASCs also formed similar structures, further supporting the potential of ASCs to develop an endothelial phenotype.

Figure 7:
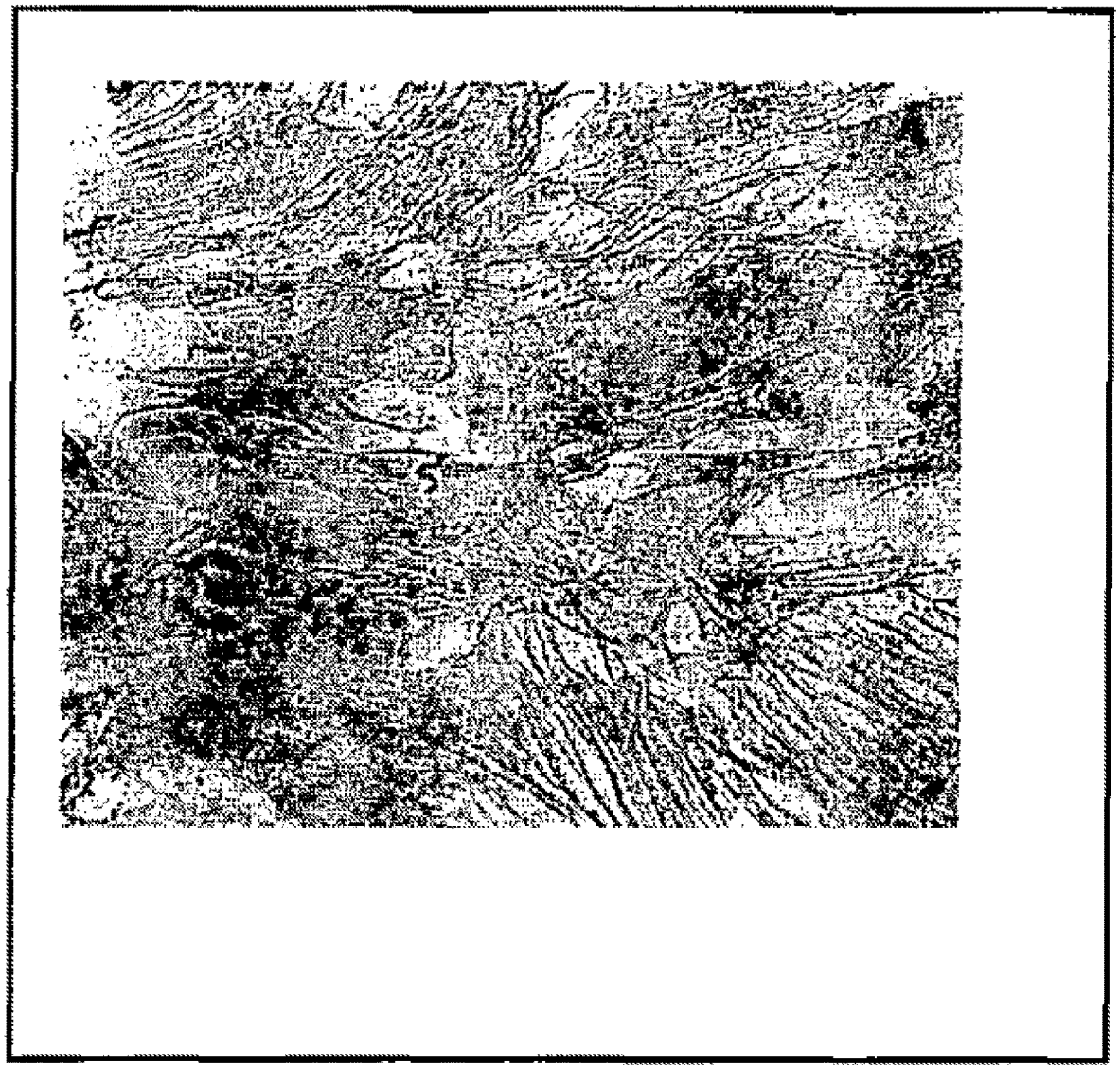
FIG. 7 shows smooth-muscle alpha-actin staining on adipose stromal cells.

In parallel studies designed to evaluate whether ASCs could also develop a smooth muscle phenotype, we stained ASCs cultured in DMEM/10% FBS media for the smooth muscle-specific marker, smooth muscle alpha-actin (FIG. 7). After culture in DMEM/10% FBS, roughly 40-50% of ASCs stain positive for alpha-actin, suggesting the development of a smooth muscle or myofibroblast phenotype. ASCs cultured in EGM2MV show essentially no cells staining positively for SM-alpha actin.

Together, these data suggest that ASCs can develop phenotypes of specific vascular cells, in a fashion that is directly responsive to their growth factor and matrix environments, suggesting a pliability of phenotype in these cells. These data demonstrate that ASCs may be able to contribute to angiogenesis or arteriogenesis directly by providing differentiated cells for incorporation into nascent vascular structures.

Example III

Secretion of Growth Factors by Adipose Derived Stromal Cells

Secretion of Angiogenic Growth Factors by ASCs

Figure 8:
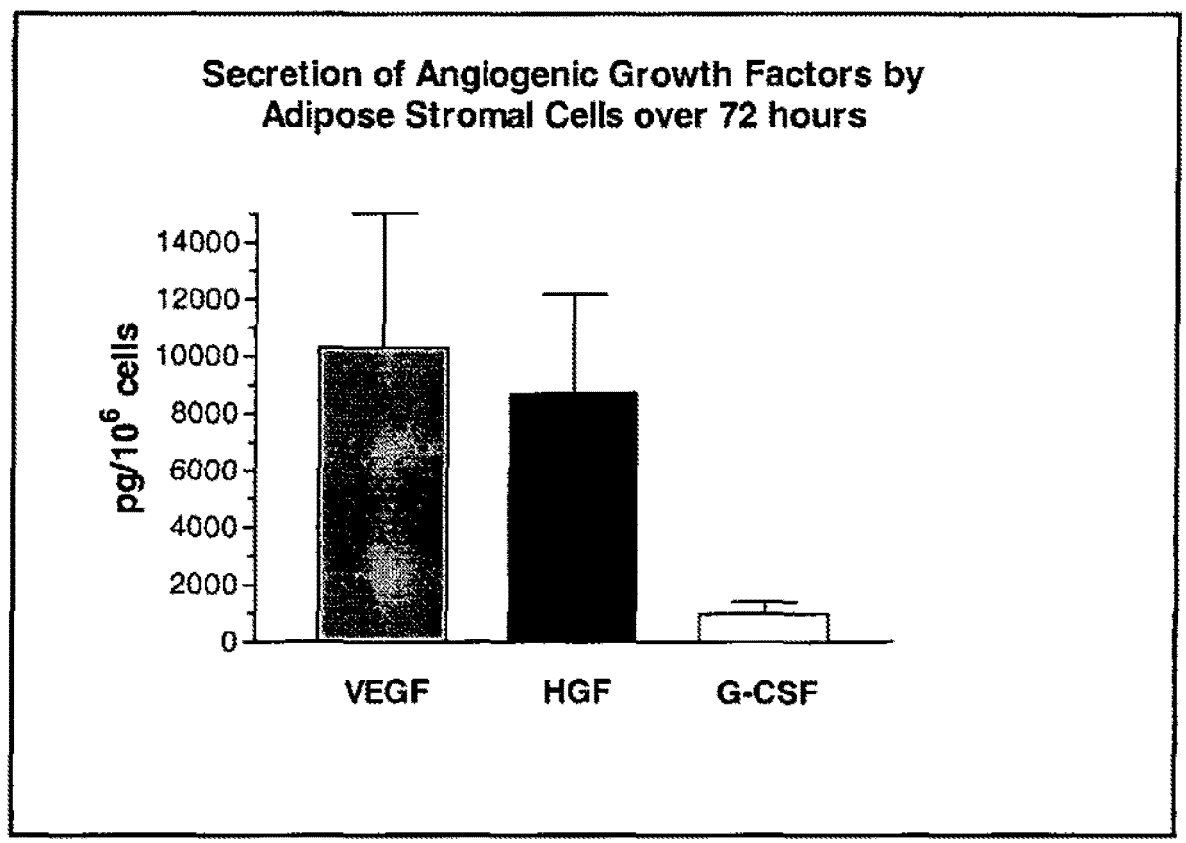
FIG. 8 is a graph which shows secretion of growth factors VEGF, HGF, and G-CSF, presented as mean+/−standard error of mean of $pg/10^6$ cells.

Since stem and progenitor cells can secrete multiple growth factors (Majka M. et al., Blood (2001) 97:3075-3085) and putative therapeutic utilities could in part be related to this endocrine function, the secretion of angiogenic growth factors by human subcutaneous ASCs was evaluated. Human subcutaneous adipose stromal cells were cultured in EGM-2-MV media to confluence, and then switched into growth-factor free basal media (EBM-2, Clonetics) for 72 hours. Cell supernatants were collected and subsequently assayed for angiogenic growth factors using ELISA and Multi-Analyte-Profiling kits (R&D Systems) for Vascular Endothelial Growth Factor (VEGF), Hepatocyte Growth Factor (HGF) and Granulocyte-Colony Stimulating Factor (G-CSF). The cell number was assessed at the end of the 72-hour period, and the secretion of growth factors is expressed in pg/$10^6$ ASCs. The cell supernatants contained significant amounts of secreted VEGF, HGF and G-CSF (FIG. 8). On the other hand, subcutaneous ASCs did not secrete detectable levels of the arteriogenic growth factor basic FGF. These findings indicate that in addition to the pluripotency of ASCs, their endocrine or paracrine potential may have significant therapeutic relevance; ASCs delivered to the heart in the setting of coronary or peripheral arterial occlusive disease, for example, may be able enhance angiogenesis not only by differentiating into a vascular phenotype, but also by recruiting resident mature vascular endothelial cells to integrate into the nascent vascular network.

Example IV

Stromal Cells can be Transfected with Mammalian Plasmids and Used for Gene Therapy Transfection of Adipose Derived Stromal Cells with Green-Fluorescent Protein (GFP)

Figure 9:
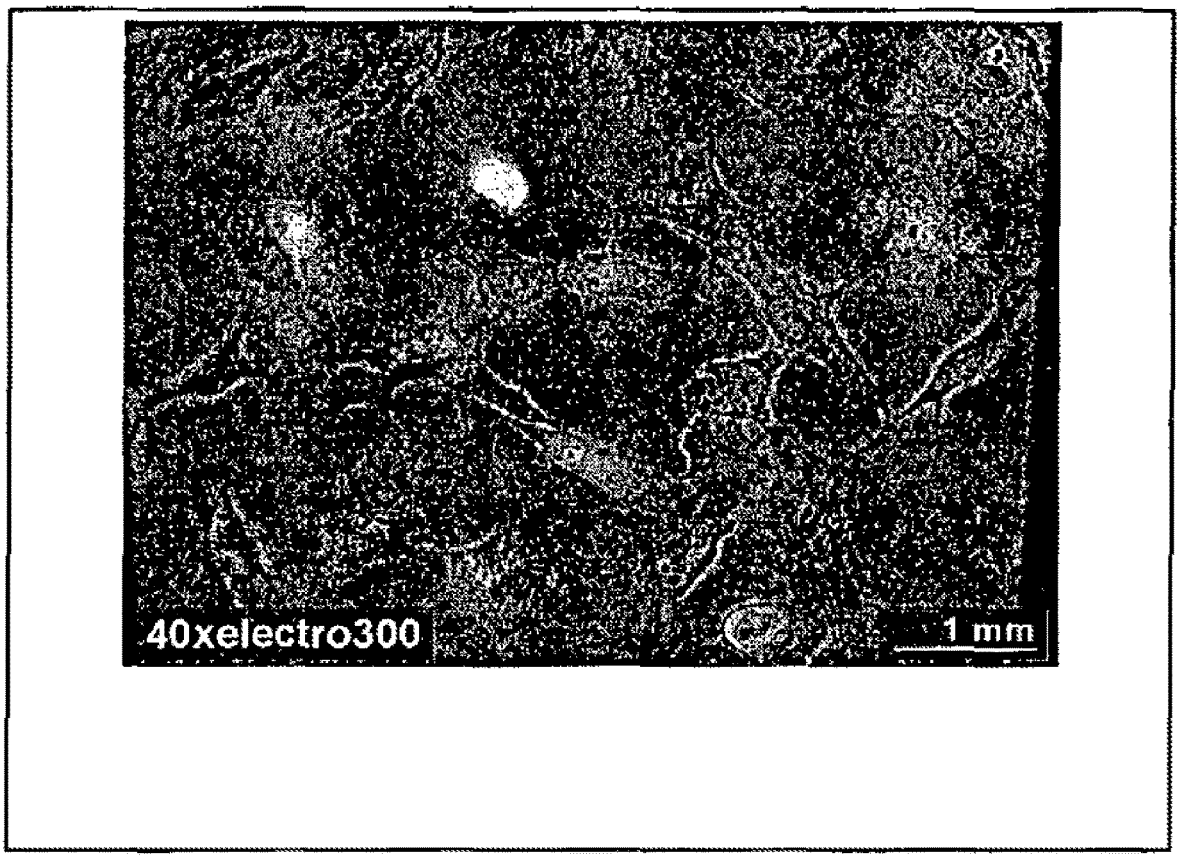
FIG. 9 is a micrograph of GFP expression on porcine adipose stromal cells. The fluorescent image is overlaid 10 on a phase contrast image.

ASCs are suitable host cells for transfection by mammalian expression plasmids, thus allowing for use of ASCs as cellular "vectors" for gene therapy. Such transfected cells should supplement the therapeutic effects of endogenously secreted growth factors. Porcine ASCs were isolated from subcutaneous porcine adipose tissue and cultured in EGM2MV media. Confluent ASC cultures at passages 0 through 4 were suspended in PBS and electroporated with green fluorescent protein (GFP) plasmid. Optimal conditions to achieve high levels of transfection were an electroporation voltage of 300V, capacitance of 9601 µF and a cell concentration of $5\times10^4$ to $1.5\times10^5$ cells per µg of DNA. Electroporated cells were plated and GFP expression was assessed on days 1-3 post transfection. Transfection efficiency as assessed by either manual counting of GFP-positive cells (FIG. 9) or by flow cytometric analysis of positive cells was routinely 50% or higher. These data show that ASCs can be transfected with non-viral methods and therefore be used as autologous cell vectors for gene therapy. This application of ASCs will be particularly beneficial in the therapeutic setting using plasmids, which encode exogenously secreted factors, which complement the activity of endogenously produced factors.

Example V

Further Characterization of Adipose Stromal Cells

Flow Cytometric Comparison of Murine ASCs and Muscle Derived Stem Cells

Figure 10:
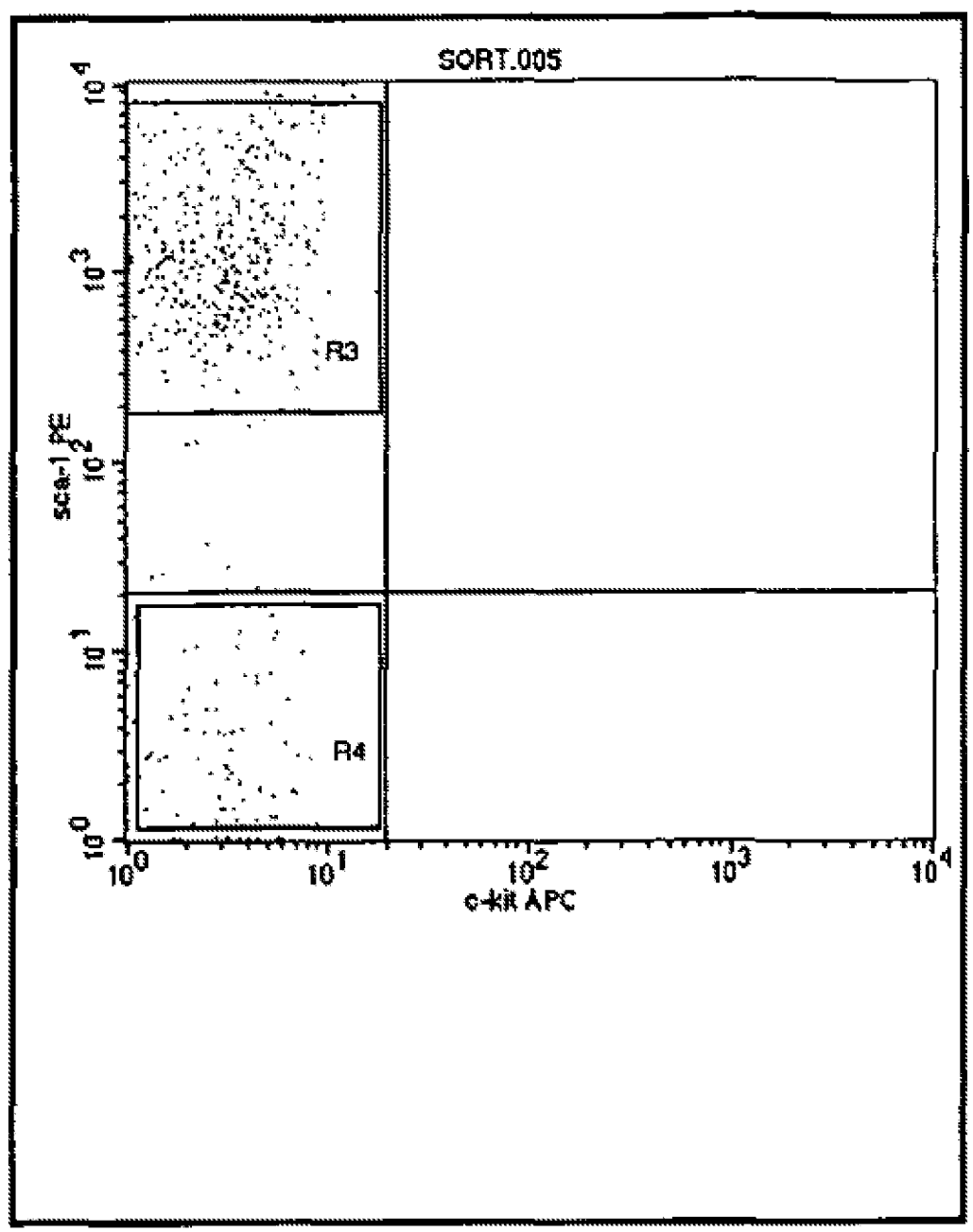
FIG. 10 shows flow cytometric analysis of murine adipose stromal cells gated on CD45(−) cells. The R3 cells are an ASC Sca-1(+)CD45(−)c-kit(−) population, while the R4 cells are Sca-1 (−)CD45 (−)c-kit(−).

Previous data indicated that the expression of Sca-1 on murine ASCs, and therefore suggested similarity between the subcutaneous ASC population and muscle derived Sca-1(+)CD45(−)c-kit(−) stem cells. The phenotype of murine ASCs was further defined by co-staining for the markers CD45 and c-kit. As shown in FIG. 10, murine ASCs contain a significant Sca-1(+)CD45(−)c-kit(−) cell population. These findings support and extend the data showing the similarity of murine ASCs and the muscle derived stem cells. This in turn provides further evidence that ASCs may have a hematopoietic potential similar to what has been shown for muscle-derived stem cells (Howell J. et al., Exp. Hem. 30:915-924, 2002).

Example VI

Further Differentiation of Adipose Derived Stromal Cells

Differentiation of Sca-1(+)CD45(−)c-Kit(−) Cells

To characterize the pluripotentiality of adipose Sca-1(+)CD45(−)c-kit(−) cells in direct comparison to that of muscle derived stem cells, Sca-1(+)CD45(−)c-kit(−) cells were purified from both tissues by cell sorting, and cultured in either neuronal or adipose differentiation media.

Figure 11A:
FIGS. 11A, 11B, 11C, 11D, and 11E show a series of micrographs (320×) taken following 12 days of culture of Sca-1(+)CD45(−)c-kit(−) cells from muscle tissue and adipose tissue, which shows adipocyte-like differentiation (Oil-Red-0 stain, FIGS. 11A and 11D) or neuron-like differentiation (phase-contrast in FIGS. 11B and 11E) when grown in the respective differentiation media.
Figure 11D:
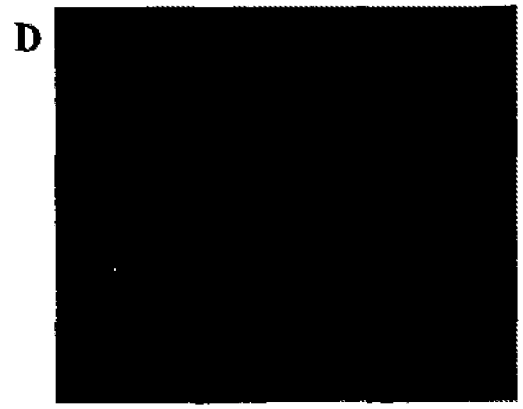
Figure 11B:
Figure 11E:
Figure 11C:

By day 12, muscle-derived Sca-1(+)CD45(−)c-kit(−) cells differentiated into adipocyte-like (with IGF-1) or neuron-like (with bFGF and PDGF) cells (FIGS. 11A and B). Neuronal differentiation of these cells was confirmed by positive staining for the tau-protein (FIG. 11C.) The similarly purified population of adipose-derived Sca-1(+)CD45(−)c-kit(−) cells also responded to these respective growth conditions by differentiating into adipocyte-like (FIG. 11D) and neuron-like cells (FIG. 11E). Staining for tau-protein for adipose-derived cells in neuronal differentiation media was not yet available at the time. Control experiments with Sca-1-negative cells did not demonstrate any significant transdifferentiation, thus showing for the first time that pluripotency of ASCs may be specifically observed in a particular sorted population. These data suggest that Sca-1(+)CD45(−)c-kit(−) cells within the uniquely accessible adipose tissue compartment, have comparable differentiation potential to similar cells derived from skeletal muscle, and thus may represent a common stem cell in multiple tissues.

Example VII

Adipose Stromal Cells can be Delivered to the Myocardium Via Retrograde Coronary Venous Delivery (RCVD) and Direct Injection Delivery of ASCs to the Myocardium of Pigs Via RCVD Juvenile farm pigs, 25-35 kg, were used. The anterior interventricular vein (AIV) or posterior vein of left ventricle (PVLV) was cannulated by a balloon-tipped catheter. The balloon was inflated to prevent venous regurgitation and myocardial blush was confirmed by 1.0-1.5 cc contrast injection.

Human adipose stromal cells, and porcine aortic endothelial cells were delivered via retrograde coronary venous delivery (RCVD.) Briefly, 5 ml of $2\times10^6$ pre-labeled human adipose stromal cells or porcine aortic endothelial cells were labeled with either PKH26 or BrdU, and administered to pigs. Animals were euthanized 1-1.5 hours post delivery.

The heart was then sliced transversely, perpendicular to the apical-basal axis. Planimetry measurement was performed using NIH Image. Cells in the area of myocardial blush were evaluated by fluorescence microscopy or immunostaining for BrdU (See FIGS. 12A-D.)

Retrograde infusion was well tolerated in all animals without adverse hemodynamic effects; the arterial pressure and heart rate did not change significantly following delivery. The retrograde infusion time was 5.6.±2.8 sec. Non-sustained ventricular tachycardia was limited to the time of retrograde infusion, consisting of 5 to 8 ectopic beats and ceasing immediately following the injection.

As shown in FIGS. 12A-D, PKH26 and BrdU pre-labeled cells were observed at the target myocardium tissue. From this example, it is clear that multiple cell types can be delivered into the myocardium using RCVD, and that RCVD results in widespread cell distribution in the myocardial tissue.

Delivery of ASCs to the Myocardium of Pigs Via Direct Injection

Figure 12A:
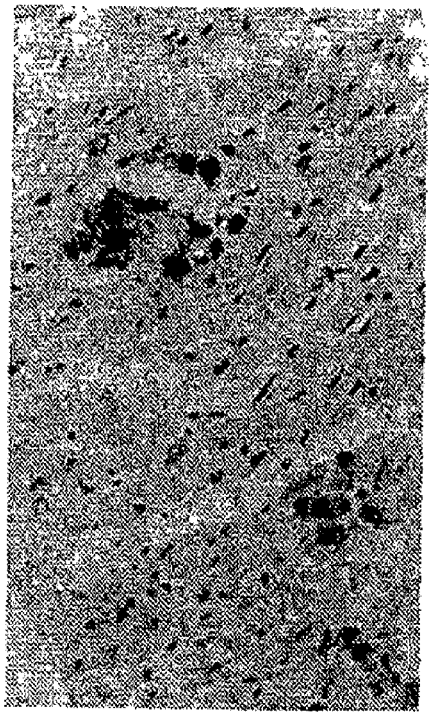
FIGS. 12A, 12B, 12C, 12D, 12E, and 12F are micrographs of porcine myocardium tissue, showing the distribution of BrdU labeled cells (marked with arrows) following administration by retrograde coronary venous delivery (FIGS. 12A-D) and by direct injection (FIGS. 12E-F).
Figure 12B:
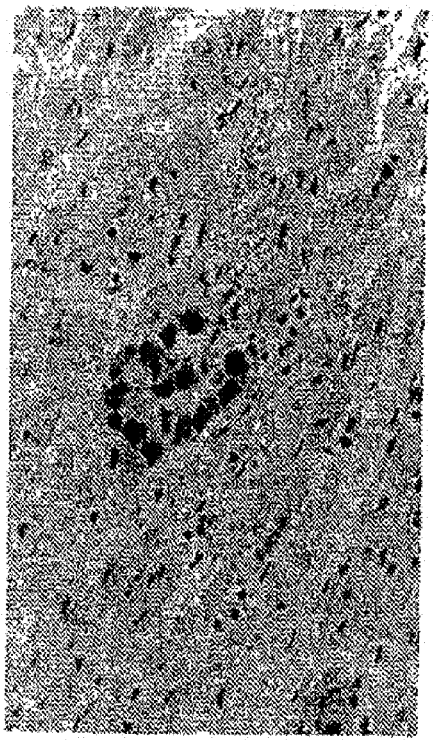
Figure 12C:
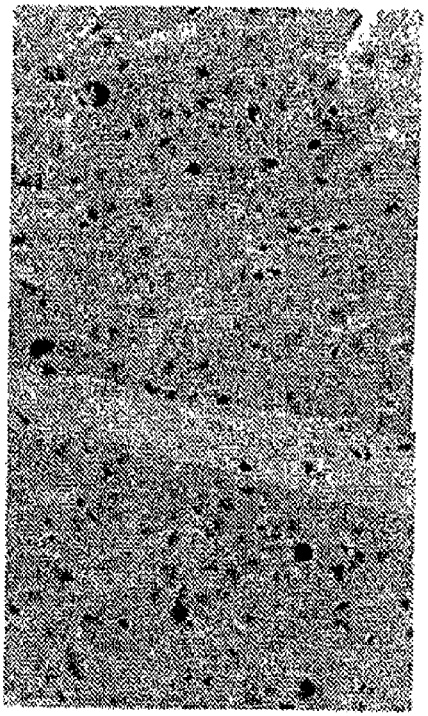
Figure 12D:
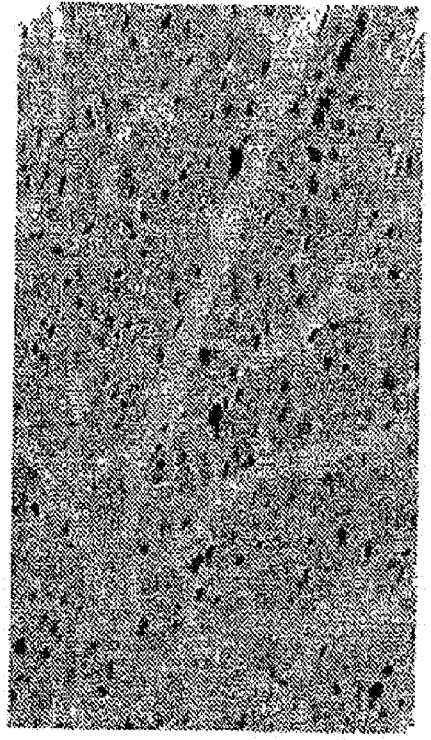
Figure 12F:
Figure 12E:
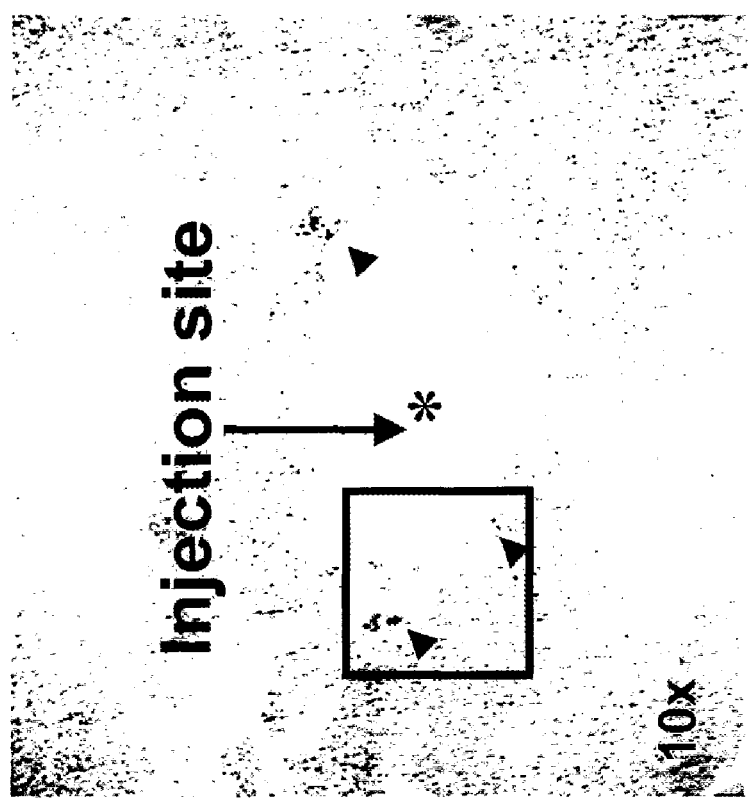

Direct Injection of BrdU and PKH26 labeled cells was performed using a tuberculine syringe. After the heart was exposed, 200 microliters of BrdU pre-labeled cell suspension containing $2\times10^5$ cells was injected into the left ventricle free wall, at nine discrete injection sites. See FIGS. 12E-F. Alternatively, cells can be injected into the ventricular muscle using needle devices which are introduced from the ventricular lumen (injection into the endocardial surface), or into veins and/or arteries coursing over the heart. These techniques for intramuscular and intravascular injection are generally known in the art.

The foregoing results demonstrate that delivery of stem cells via RCVD gives rise to a wider distribution of cells in target tissue than direct microinjection.

Example VIII

An In Vivo Model for Assessment of Angiogenesis

In Vivo Assessment of Angiogenesis Using a Mouse Hindlimb Ischemia Model

An in vivo model of quantifying angiogenesis over time has been established in a mouse model using hindlimb ischemia. This has allowed identification of modulators of angiogenesis. In one study, for example, the role of the GTP-binding signalling molecule Rac2 was evaluated. Wild-type mice (C57BL6) and Rac2-/- mice underwent ligation of the femoral artery below the inguinal ligament.

Figure 13A:
FIGS. 13A and 13B show laser Doppler imaging of the mouse hindlimb, which demonstrates that the Rac −/− mouse (FIG. 13A) has persistent marked impairment of the ischemic leg (right leg) perfusion, whereas the wild-type mouse (FIG. 13B) shows significant restoration of blood perfusion to the ischemic leg (right leg.) High or normal blood perfusion is depicted in red, and low or absent perfusion is shown in yellow and green.
Figure 13B:
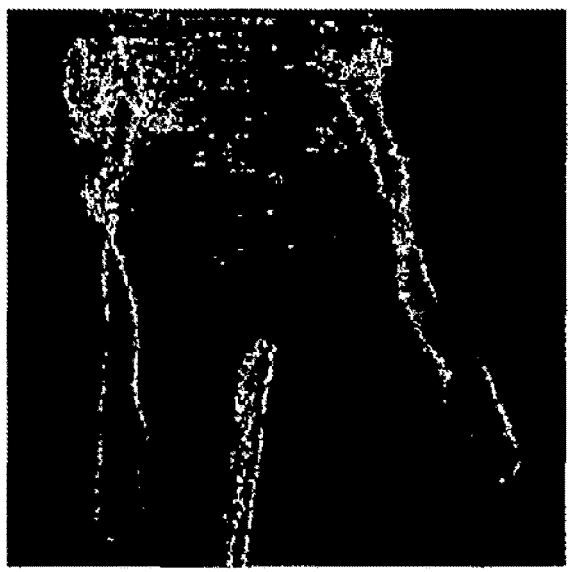

Non-invasive laser doppler imaging (LDI) (Moor Instruments) was performed on the ischemic and non-ischemic hindlimbs of all mice on post-operative days 1, 4, 7, 10, 14 and 21, in order to evaluate blood flux as a surrogate for perfusion. A representative LDI image is shown in FIG. 13, where the Rac2-/- mouse has significant impairment of blood flow to the ischemic leg (Panel 13A), manifested by a blue shift in the colors of the pseudocolored pixels, while the wild-type mouse has recovered most of the perfusion to the ischemic leg, reflected by a bilaterally symmetric flux reflected in the pseudocolor image.

Figure 14:
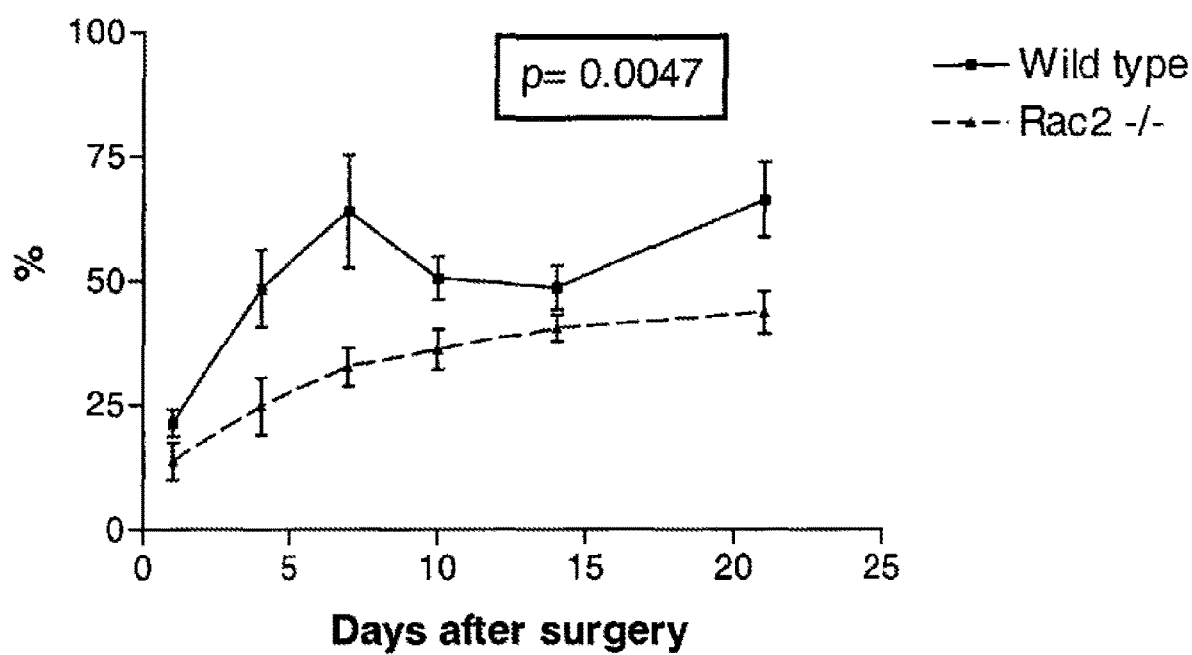
FIG. 14 shows the ratio of perfusion to the ischemic leg to that of the non-ischemic leg measured by laser Doppler imaging in wild-type and Rac2−/− mice.

When the blood perfusion is measured over time and quantitated as a ratio of blood perfusion in the ischemic to the non-ischemic leg, it becomes apparent that the impairment in recovery of limb perfusion in Rac2-/- mice when compared to wild-type mice is first evident on post-surgery day 4 (FIG. 14). This difference between the two groups is maintained through day 21. Statistical analysis using a between group repeated measures ANOVA shows a highly significant between group difference. This repeated in vivo assessment of angiogenesis allows one to not only distinguish between global angiogenesis in a control and treatment group, but also to observe time-dependent changes. This model system can be used to quantify the effects of ASC transplantation into ischemic mouse hindlimbs on time-dependent angiogenesis.

Intramuscular Injection of ASCs into Ischemic Hindlimbs Improves Perfusion

Figure 15A:
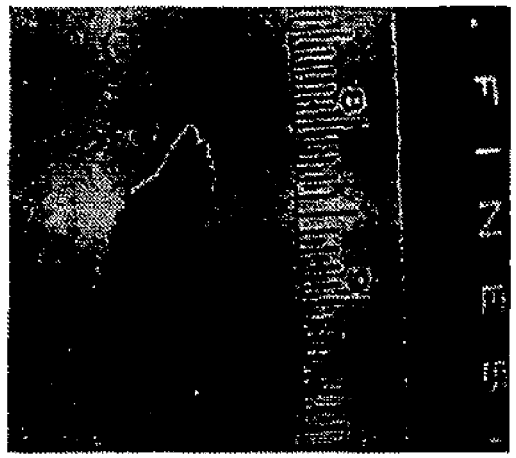
FIGS. 15A and 15B show a representative depiction of limb necrosis on day 10 in a media injected mouse (FIG. 15A) and an adipose stromal cell injected mouse (FIG. 15B), which shows that adipose stromal cell injection can attenuate ischemia-induced necrosis.
Figure 15B:
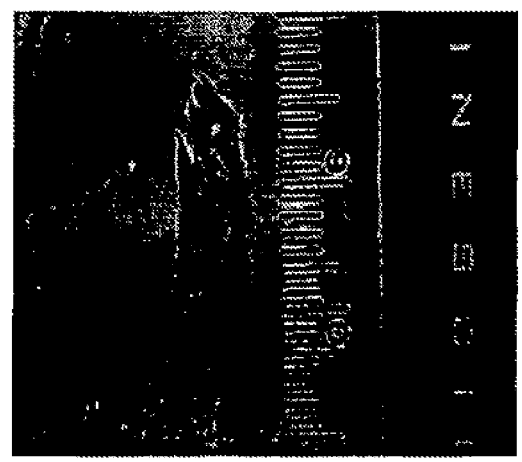
Figure 16:
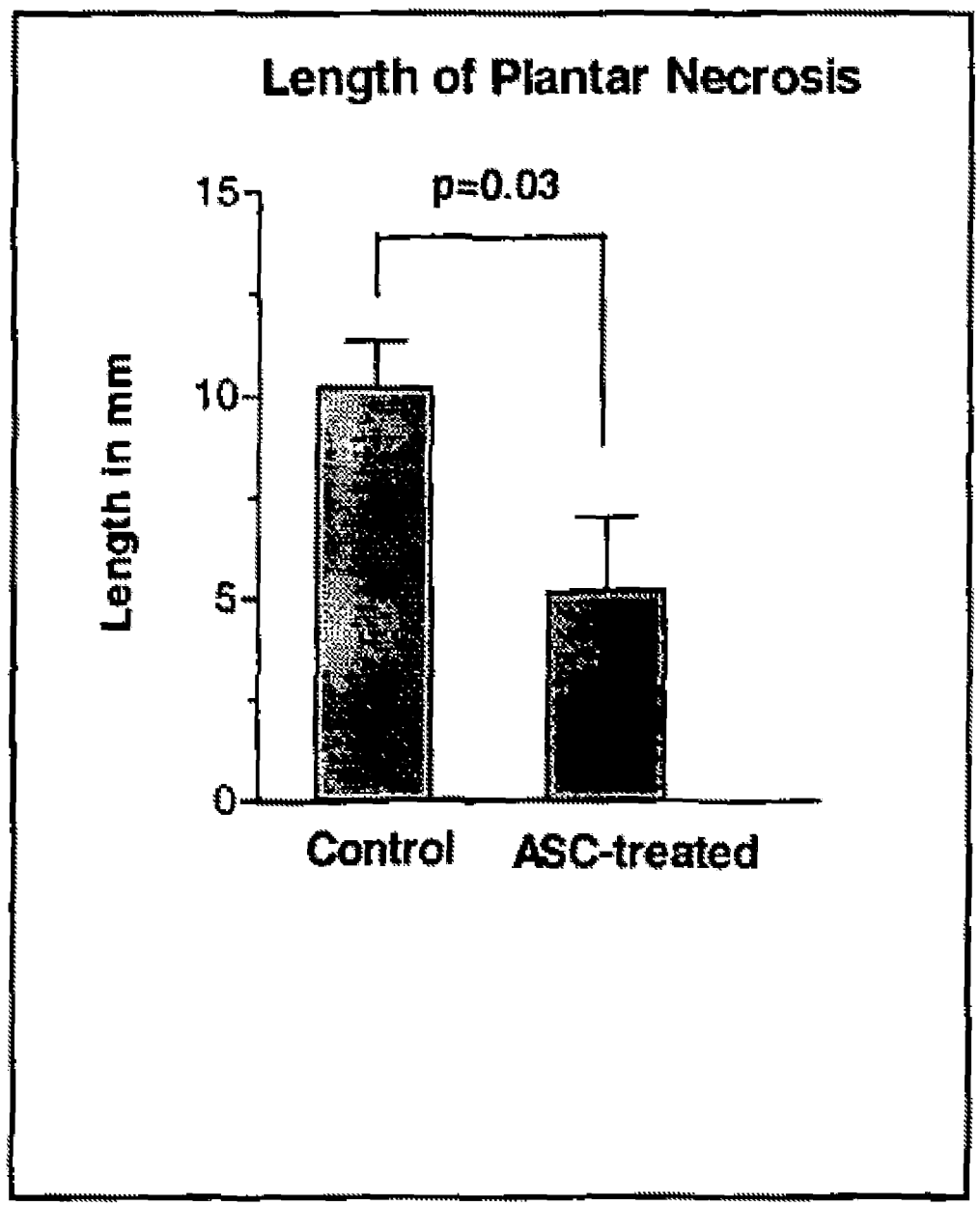
FIG. 16 is a graph showing that on day 10, adipose stromal cell treated animals had a significantly reduced degree of limb necrosis when compared to the control media injected mice.

Human ASCs were isolated and cultured in the presence of endothelial growth media (EGM-2-MV, Clonetics) containing the growth factors VEGF, bFGF, EGF and IGF. NOD/SCID immune deficient mice (n=6, aged 8 months) underwent unilateral femoral artery ligation and received intramuscular injection of either $4\times10^5$ human ASCs per mouse (n=3) or media (n=3) into the quadriceps, gastrocnemius and tibialis muscles of the ischemic hindlimb on the subsequent day. Due to the advanced age of the mice and the reduced immunologic competence, the endogenous angiogenesis response of the mice was markedly blunted, thus resulting in some degree of either toe or limb necrosis in all animals. However, by day 10 of the study, mice receiving ASC injections had a remarkably mitigated extent of limb necrosis (FIG. 15). This reduction in necrosis was statistically significant (FIG. 16).

This study highlights the in vivo angiogenic potential of the cells. An ongoing hindlimb ischemia experiment with younger NOD/SCID mice has not resulted in any significant toe or limb necrosis, thus allowing us to use Laser Doppler Imaging to detect subtle perfusion differences between cell-treated and media-treated animals.

The cells disclosed herein may optionally be administered by retrograde coronary venous delivery, or other means set forth above.

In conclusion, these preliminary data support the hypotheses of our original proposal that ASCs have a phenotype and pluripotentiality that is similar to that of muscle-derived stem cells and that they can accordingly be used for cell therapies targeted at enhancing angiogenesis and hematopoiesis. The key advantage of identifying such cells in subcutaneous adipose tissue is that they can be harvested by liposuction and therefore increase the clinical feasibility of autologous cell therapy.

The previous examples and description set forth certain embodiments of the present disclosure. It should be appreciated that not all components or method steps of a complete implementation of a practical system are necessarily illustrated or described in detail. Rather, only those components or method steps necessary for a thorough understanding of the present disclosure have been illustrated and described in detail. Actual implementations may utilize more steps or components or fewer steps or components. Thus, while certain of the preferred embodiments of the present disclosure have been described and specifically exemplified above, it is not intended that the present disclosure be limited to such embodiments. Various modifications may be made thereto without departing from the scope and spirit of the present disclosure, as set forth in the following claims.

The invention claimed is:

1. A method for isolating adipose derived stromal cells from a human patient comprising:
    a) performing adipose tissue resection or suction on said patient;
    b) dissecting tissue obtained from said tissue resection or suction and dissociating said tissue into a cell suspension;
    c) removing adipocytes from said cell suspension;
    d) culturing the adipocyte-depleted cell suspension in media containing vascular endothelial growth factor (VEGF), basic fibroblast growth factor (bFGF), epidermal growth factor (EGF), and insulin-like growth factor (IGF); and
    e) isolating adipose derived stromal cells secreting VEGF, hepatocyte growth factor (HGF), and granulocyte-colony stimulating factor (G-CSF).

2. The method of claim 1, further comprising culturing the cells of step e) in DMEM.

3. The method of claim 1, further comprising culturing the cells of step e) in DMEM and 10% fetal bovine serum (FBS).

4. The method of claim 1, further comprising culturing the cells of step e) in media containing a receptor ligand cocktail, said ligands being selected from the group consisting of at least one of VEGF, LIF, bFGF, IGF1, IGF2, HGF, cardiotrophin, myotrophin, nitric oxide synthase 1, nitric oxide synthase 2, nitric oxide synthase 3, tumor necrosis factor alpha, tumor necrosis factor beta, fibroblast growth factor, pleotrophin, endothelin, and angiopoietin.

5. The method of claim 1, wherein the adipose derived stromal cells do not secrete detectable levels of basic fibroblast growth factor (bFGF).

6. The method of claim 1, further comprising the step, subsequent to step d) and prior to step e), of culturing the cell suspension in a growth-factor free basal medium.

7. The method of claim 6, wherein the growth-factor free basal medium is EBM2.

8. The method of claim 1, wherein the dissociating step is performed using agitation, sonic energy, or thermal energy.

9. The method of claim 1, wherein the dissociating step is performed using collagenase, dispase, or trypsin.

10. The method of claim 1, further comprising introduction of an exogenous nucleic acid molecule encoding a protein of interest into the mixed population of cells of step c).

11. The method of claim 1, further comprising exposing the cell suspension in step b) to red cell lysis buffer.

* * * * *